(12) United States Patent
Aberman

(10) Patent No.: US 9,175,262 B2
(45) Date of Patent: Nov. 3, 2015

(54) ADHERENT CELLS FROM PLACENTA AND USE OF SAME IN DISEASE TREATMENT

(75) Inventor: Zami Aberman, Tel-Mond (IL)

(73) Assignee: Pluristerm Ltd., Haifa (IL)

( * ) Notice: Subject to any disclaimer, the term of this patent is extended or adjusted under 35 U.S.C. 154(b) by 0 days.

(21) Appl. No.: 13/512,503

(22) PCT Filed: Nov. 29, 2010

(86) PCT No.: PCT/IB2010/003219
§ 371 (c)(1),
(2), (4) Date: Sep. 12, 2012

(87) PCT Pub. No.: WO2011/064669
PCT Pub. Date: Jun. 3, 2011

(65) Prior Publication Data
US 2013/0004465 A1    Jan. 3, 2013

Related U.S. Application Data

(60) Provisional application No. 61/272,985, filed on Nov. 30, 2009, provisional application No. 61/371,459, filed on Aug. 6, 2010.

(51) Int. Cl.
*C12N 5/071* (2010.01)
*A61K 35/50* (2015.01)
*C12N 5/073* (2010.01)
*A61K 35/12* (2015.01)

(52) U.S. Cl.
CPC .............. *C12N 5/0605* (2013.01); *A61K 35/50* (2013.01); *A61K 2035/122* (2013.01); *C12N 2502/02* (2013.01)

(58) Field of Classification Search
CPC .. C12N 5/0605; C12N 2502/02; A61K 35/50; A61K 2035/122
USPC .................................. 424/93.7; 435/404, 325
See application file for complete search history.

(56) References Cited

U.S. PATENT DOCUMENTS

| 6,911,201 | B1 | 6/2005 | Merchav et al. |
|---|---|---|---|
| 7,534,609 | B2 | 5/2009 | Merchav et al. |
| 7,678,573 | B2 | 3/2010 | Merchav et al. |
| 8,524,496 | B2 | 9/2013 | Meiron et al. |
| 8,529,888 | B2 | 9/2013 | Meiron et al. |
| 2005/0176143 | A1 | 8/2005 | Merchav et al. |
| 2005/0181504 | A1 | 8/2005 | Merchav et al. |
| 2009/0004738 | A1 | 1/2009 | Merchav et al. |
| 2010/0209403 | A1 | 8/2010 | Meiron et al. |
| 2011/0129447 | A1 | 6/2011 | Meretzki et al. |
| 2011/0129486 | A1 | 6/2011 | Meiron |
| 2011/0171182 | A1 | 7/2011 | Abelman |
| 2011/0256108 | A1 | 10/2011 | Meiron et al. |
| 2011/0256159 | A1 | 10/2011 | Meiron et al. |
| 2011/0256160 | A1 | 10/2011 | Meiron et al. |
| 2011/0293583 | A1 | 12/2011 | Aberman |
| 2012/0122220 | A1 | 5/2012 | Merchav et al. |
| 2013/0004465 | A1 | 1/2013 | Aberman |
| 2013/0039892 | A1 | 2/2013 | Aberman |
| 2013/0259843 | A1 | 10/2013 | Duda et al. |
| 2013/0323213 | A1 | 12/2013 | Meiron et al. |
| 2013/0337558 | A1 | 12/2013 | Meiron et al. |
| 2014/0017209 | A1 | 1/2014 | Aberman et al. |
| 2014/0030805 | A1 | 1/2014 | Kasuto et al. |
| 2014/0242039 | A1 | 8/2014 | Meiron et al. |
| 2015/0125138 | A1 | 5/2015 | Duda et al. |

FOREIGN PATENT DOCUMENTS

| EP | 2 806 023 A2 | 11/2014 |
|---|---|---|
| WO | WO 2007/108003 | 9/2007 |
| WO | WO 2007-108003 A3 | 9/2007 |
| WO | WO 2008/100498 | 8/2008 |
| WO | WO 2008-100498 A3 | 8/2008 |

OTHER PUBLICATIONS

In'tAnker et al., Isolation of mesenchymal stem cells of fetal or maternal origin from human placenta. Stem Cells, vol. 22 (2004) pp. 1338-1345.*
In't Anker et al., Isolation of mesenchymal stem cells of fetal or maternal origin from human placenta. Stem Cells, vol. 22 No. 7 (Dec. 2004) pp. 1338-1345.*
Kanematsu et al., Isolation and cellular properties of mesenchymal cells derived from the decidua of human germ placenta. Differentiation, vol. 82 (2011) pp. 77-88.*
Santos et al., Multidisciplinary utilization of dimethyl sulfoxide: pharmacological, cellular, and molecular aspects. Biochemical Pharmacology, vol. 65, No. 7 (Apr. 1, 2003) pp. 1035-1041.*

(Continued)

*Primary Examiner* — Laura Schuberg
*Assistant Examiner* — Kara Johnson
(74) *Attorney, Agent, or Firm* — Wolf, Greenfield & Sacks, P.C.

(57) ABSTRACT

Methods for treating conditions by administration of placenta derived adherent stromal cells to a subject in thereof are provided. Such conditions include skeletal muscle defects, neuropathic pain, and myocardial infarction. Also provided are methods wherein the adherent stromal cells administered are cultured under 2 dimensional or 3 dimensional growth conditions. Also provided are methods in which the cells administered are at least 70% adherent cells from a maternal or fetal portion of the placenta.

21 Claims, 17 Drawing Sheets

(56) References Cited

OTHER PUBLICATIONS

R. Ian Freshney, "Cryopreservation." in: Culture of Animal Cells: A Manual of Basic Technique and Specialized Applications Sixth Edition (John Wiley & Sons, Inc. Hoboken, NJ, online Mar. 9, 2011) pp. 317-334, 2010.*

In't Anker et al. "Isolation of Mesenchymal Stem Cells of Fetal or Maternal Origin from Human Placenta," Stem Cells, XP002581690, 22(7): 1338-1345, Jan. 1, 2004.

Li et al. "Mesenchymal Stem Cells Derived from Human Placenta Suppress Allogenic Umbilical Cord Blood Lymphocyte Proliferation," Cell Research, XP009080356, 15(7): 539-547, Jul. 1, 2005.

Huang et al. "Isolation of Mesenchymal Stem Cells from Human Placental Decidua Basalis and Resistance to Hypoxia and Serum Deprivation", Stem Cell Reviews and Reports, XP002635213, 5(3): 247-255, Sep. 2009.

"Pluristem Demonstrates the Potential of its PLX Cells to Treat Crohn's Disease and Ulcerative Colitis", Internet Citation, XP002553068, URL: http://80.244.168.41/$sitepreview/pluristem.com/28_05_2008.asp, May 28, 2008.

Parolini et al. "Concise Review: Isolation and Characterization of Cells from Human Term Placenta: Outcome of the First International Workshop on Placenta Derived Stem Cells", Stem Cells, XP002567088, 26(2): 300-311, Feb. 1, 2008.

Partial European Search Report mailed Oct. 21, 2014 for Application No. EP 14 17 0266.

Freshney; "Culture of Animal Cells—A Manual of Basic Technique", Fourth Edition; Biology of Cultured Cells; Chapter 2; pp. 9-16, 2000.

Freshney; "Culture of Animal Cells—A Manual of Basic Technique", Fourth Edition; Differentiation; Chapter 16; pp. 259-267, 2000.

Matziolis et al., "Autologous Bone Marrow-Derived Cells Enhance Muscle Strength Following Skeletal Muscle Crush Injury in Rats", Tissue Engineering, 2006; 12:2, pp. 361-367.

Pieternella et al., "Isolation of Mesenchymal Stem Cells of Fetal or Maternal Origin from Human Placenta," Stem Cells, 2004; 22:1338-1345.

Yen et al., "Isolation of Multipotent Cells from Human Term Placenta", Stem Cells; 2005; 23:3-9.

* cited by examiner

Figs. 2A-C

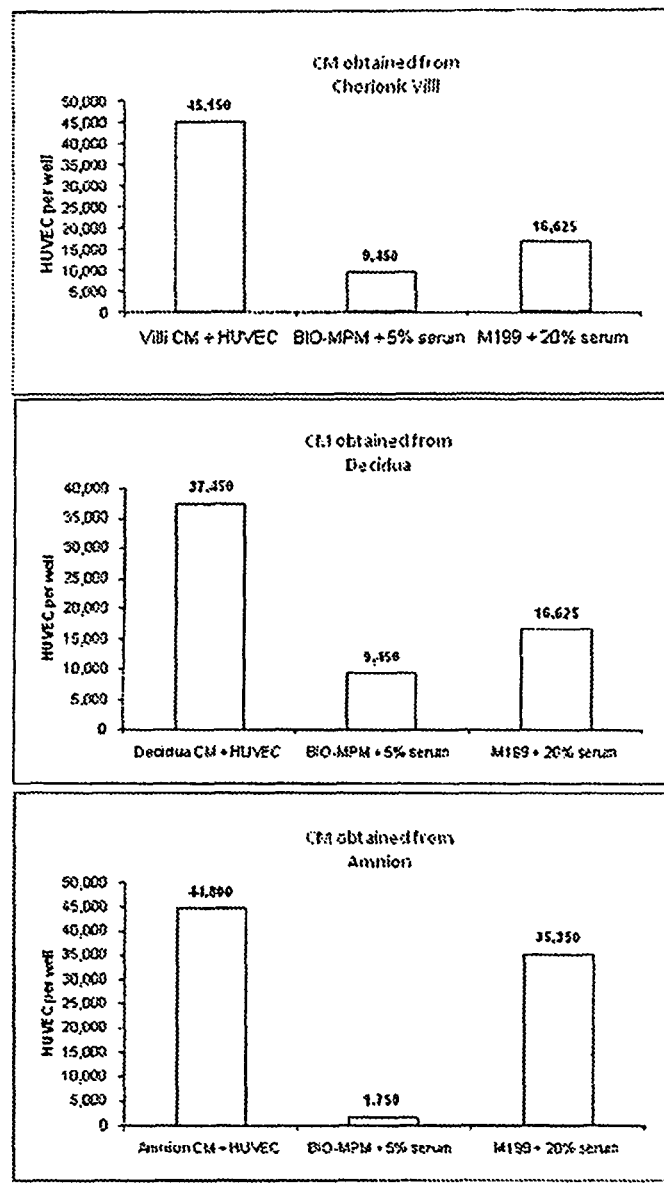
Figs. 6A-C

ADHERENT CELLS FROM PLACENTA AND USE OF SAME IN DISEASE TREATMENT

RELATED APPLICATIONS

This application is a national stage application of International Application No. PCT/IB2010/003219, filed Nov. 29, 2010, which claims priority to U.S. Provisional Application No. 61/272,985, filed Nov. 30, 2009 and U.S. Provisional Application No. 61/371,459, filed Aug. 6, 2010, the disclosures of which are incorporated by reference in their entirety.

FIELD AND BACKGROUND OF THE INVENTION

The present invention, in some embodiments thereof, relates to adherent cells from placenta and use of same in disease treatment.

In recent years, considerable activity has focused on the therapeutic potential of mesenchymal stromal cells (MSCs) for various medical applications including tissue repair of damaged organs such as the brain, heart, bone and liver and in support of bone marrow transplantations (BMT). MSCs, a heterogeneous population of cells obtained from e.g. bone marrow, adipose tissue, placenta, and blood, are capable of differentiating into different types of cells (e.g. reticular endothelial cells, fibroblasts, adipocytes, osteogenic precursor cells) depending upon influences from various bioactive factors. Accordingly, MSCs have been widely studied in regenerative medicine as the foundation to build new tissues such as bone, cartilage and fat for the repair of injury or replacement of pathologic tissues and as treatment for genetic and acquired diseases [Fibbe and Noort, Ann N Y Acad Sci (2003) 996: 235-44; Horwitz et al., Cytotherapy (2005) 7(5): 393-5; Zimmet and Hare, Basic Res Cardiol (2005) 100(6): 471-81]. Furthermore, the multipotent ability of MSCs, their easy isolation and culture, as well as their high ex vivo expansion potential make them an attractive therapeutic tool [Fibbe and Noort, supra; Minguell et al. Exp Biol Med (Maywood) (2001) 226(6): 507-20].

An emerging body of data indicates that MSCs escape recognition of alloreactive cells and are considered to be immune privileged [Le Blanc et al., Exp Hematol (2003) 31(10): 890-6]. Having low immunogenicity, MSCs are not rejected by the patient's immune system and therefore are considered not to require HLA matching.

Placental derived MSCs exhibit many markers common to MSCs isolated from other tissues, e.g. CD105, CD73, CD90 and CD29, and the lack of expression of hematopoietic, endothelial and trophoblastic-specific cell markers. Adipogenic, osteogenic, and neurogenic differentiation have been achieved after culturing placental derived MSCs under appropriate conditions [Yen et al., Stem Cells (2005) 23(1): 3-9]. Furthermore, MSCs isolated from placenta and cultured in vitro have been demonstrated to be immune privileged in a similar fashion as MSCs [Li et al., Cell Res (2005) 15(7): 539-47]. Thus, the placenta provides an ethically non-controversial and easily accessible source of MSCs for experimental and clinical applications [Zhang et al., Exp Hematol (2004) 32(7): 657-64].

SUMMARY OF THE INVENTION

According to an aspect of some embodiments of the present invention there is provided purified populations of adherent cells from the placenta, a conditioned media prepared from any of the populations of adherent cells described herein that can be used for treating a condition which can benefit from cell or organ transplantation.

According to some embodiments of the invention, the adherent cells comprise a positive marker expression selected from the group consisting of CD73, CD90, CD29, CD105 and D7-fib; that is, in some embodiments the adherent cells express one or more of CD73, CD90, CD29, CD105 or D7-fib.

According to some embodiments of the invention, the adherent cells comprise a negative marker expression selected from the group consisting of CD3, CD4, CD45, CD80, HLA-DR, CD11b, CD14, CD19, CD34, CD31, CD200, KDR, and CD79; that is, in some embodiments the adherent cells do not express CD3, CD4, CD45, CD80, HLA-DR, CD11b, CD14, CD19, CD34, CD31, CD200, KDR, or CD79.

According to some embodiments of the invention, the adherent cells are cultured in a three-dimensional (3D) culture.

According to some embodiments of the invention, the three-dimensional (3D) culture comprises a 3D bioreactor.

According to some embodiments of the invention, culturing of the adherent cells in the 3D culture is effected under perfusion.

According to some embodiments of the invention, culturing of the adherent cells is effected for at least 3 days.

According to some embodiments of the invention, culturing of the adherent cells is effected until at least 10% of the adherent cells are proliferating.

According to some embodiments of the invention, the adherent cells are cultured in a two-dimensional (2D) culture.

According to some embodiments of the invention, at least 10% of the adherent cells are at a proliferative state; that is, at least 10% of the adherent cells are proliferating.

According to some embodiments of the invention, the adherent cells are less committed to an osteogenic lineage as compared to adherent cells from bone marrow grown and allowed to differentiate under the same conditions.

According to some embodiments of the invention, the adherent cells are less committed to an adipogenic lineage as compared to adherent cells from bone marrow grown and allowed to differentiate under the same conditions.

According to an aspect of some embodiments of the present invention there is provided a population of adherent cells derived from the placenta, wherein the population comprises at least 70% adherent cells from a maternal portion of the placenta.

According to some embodiments of the invention, the maternal portion of the placenta comprises decidua basalis, decidua parietalis, or both decidua basalis and decidua parietalis.

According to an aspect of some embodiments of the present invention there is provided a population of adherent cells derived from the placenta, wherein the population comprises at least 70% adherent cells from a fetal portion of placenta.

According to some embodiments of the invention, the fetal portion of the placenta comprises amnion.

According to some embodiments of the invention, the fetal portion of the placenta consists of amnion.

According to some embodiments of the invention, the fetal portion of the placenta comprises chorionic villi.

According to some embodiments of the invention, the fetal portion of the placenta consists of chorionic villi.

According to some embodiments of the invention, population of cells is a population in wherein not more than 3.5%, not more than 3%, not more than 2%, or not more than 1% of the population of adherent cells from a maternal portion express CD200 as measured by flow cytometry using an isotype control to define negative expression.

According to some embodiments of the invention, the adherent cells comprise a cell diameter which is smaller than that of adherent cells derived from a fetal portion of placenta.

According to some embodiments of the invention, the adherent cells comprise a cell proliferation capacity which is higher than that of adherent cells derived from a fetal portion of placenta.

According to some embodiments of the invention, the adherent cells are capable of suppressing an immune reaction to a lesser extent than adherent cells from a fetal portion of placenta when tested in a mixed lymphocyte culture.

According to an aspect of some embodiments of the present invention there is provided a conditioned medium isolated from a culture comprising any of the above populations of cells.

According to an aspect of some embodiments of the present invention there is provided a pharmaceutical composition comprising as an active ingredient any of the population of cells described herein or any of the conditioned media described herein and a pharmaceutically acceptable carrier.

According to an aspect of some embodiments of the present invention there is provided a method of treating a medical condition that can benefit from cell or organ transplantation comprising administering to a subject in need thereof a therapeutically effective amount of any of the pharmaceutical compositions described herein, thereby treating the subject.

According to an aspect of some embodiments of the present invention there is provided use of any of the population of cells or the conditioned medium described herein, for the manufacture of a medicament for treating a condition which can benefit from cell or organ transplantation.

According to some embodiments of the invention, the condition is selected from the group consisting of ischemia, peripheral arterial disease (PAD), critical limb ischemia (CLI), lower extremity ischemia, stroke, ischemic vascular disease, vascular disease of the kidney, ischemic heart disease, myocardial ischemia, coronary artery disease (CAD), atherosclerotic cardiovascular disease, left main coronary artery disease, arterial occlusive disease, peripheral ischemia, peripheral vascular disease, arteriosclerosis, retinopathy, retinal repair, remodeling disorder, von Hippel-Lindau syndrome, hereditary hemorrhagic telengiectasiaischemic vascular disease, Buerger's disease, ischemic renal disease, ischemic placenta, reproduction associated disorders, graft-versus-host disease, solid organ transplantation, hematopoietic stem cell transplantation, diabetes, connective tissue damage, cancer, pre-cancer, bone cancer, osteosarcoma, bone metastases, bone fracture, burn wound, articular cartilage defect, deep wound, delayed wound-healing, delayed ulcer healing, subchondral-bone cyst, osteoporosis, osteoarthritis, degenerated bone, cartilage damage, articular cartilage defect, injured tendons, autoimmune diseases, metabolic disorders, psoriasis, neuropathic pain, peripheral nerve injury, neurodegenerative disease, support of kidney transplantation and inflammatory diseases.

According to some embodiments of the invention, the condition is selected from the group consisting of heart failure, myocardial infarction, neuropathic pain, skeletal muscle defect, stroke, and ischemic heart disease.

According to an aspect of some embodiments of the invention, the method is a method of treating a skeletal muscle defect comprising administering to a subject in need thereof a therapeutically effective amount of composition comprising placenta derived adherent stromal cells, thereby treating the skeletal muscle defect.

According to an aspect of some embodiments of the invention, the method is a method of treating neuropathic pain comprising administering to a subject in need thereof a therapeutically effective amount of composition comprising placenta derived adherent stromal cells, thereby treating the neuropathic pain.

According to some embodiments of the invention, the neuropathic pain is associated with inflammatory pain, diabetic polyneuropathy, human immunodeficiency virus (HIV) sensory neuropathy, poststroke syndromes, ischemia, or multiple sclerosis.

According to an aspect of some embodiments of the invention, the method is a method of treating myocardial infarction comprising administering to a subject in need thereof a therapeutically effective amount of composition comprising placenta derived adherent stromal cells, thereby treating the myocardial infarction.

According to an aspect of some embodiments of the invention there is provided a use of a composition comprising placenta derived adherent stromal cells for the manufacture of a medicament for treating a skeletal muscle defect, neuropathic pain, myocardial infarction.

According to an aspect of some embodiments of the invention there is provided a pharmaceutical composition comprising as an active ingredient placenta derived adherent stromal cells for use in treating a skeletal muscle defect, neuropathic pain, or myocardial infarction.

According to some embodiments of the invention, the pharmaceutical composition is a pharmaceutical composition for treating neuropathic pain that is associated with inflammatory pain, diabetic polyneuropathy, human immunodeficiency virus (HIV) sensory neuropathy, poststroke syndromes, ischemia, or multiple sclerosis.

According to some embodiments of the invention, the adherent cells express one or more of CD73, CD90, CD29, CD105 or D7-fib.

According to some embodiments of the invention, the adherent cells do not express CD3, CD4, CD45, CD80, HLA-DR, CD11b, CD14, CD19, CD34, CD31, CD200, CD271, KDR, or CD79.

According to some embodiments of the invention, the adherent cells express one or more of beta-Endorphin, dynorphin A, leu-enkephalin, or met-enkephalin.

According to some embodiments of the invention, the adherent cells suppress T cell activity.

According to some embodiments of the invention, the adherent cells comprise at least 70% adherent cells from a maternal portion of the placenta.

According to some embodiments of the invention, not more than 3.5%, not more than 3%, not more than 2%, or not more than 1% of the adherent cells from a maternal portion express CD200 as measured by flow cytometry using an isotype control to define negative expression.

According to some embodiments of the invention, the maternal portion of the placenta comprises decidua basalis, decidua parietalis, or both decidua basalis and decidua parietalis.

According to some embodiments of the invention, the adherent cells are produced by culture using 3D culture conditions.

According to some embodiments of the invention the three-dimensional (3D) culture comprises a 3D bioreactor.

According to an aspect of some embodiments of the invention, the 3D culture is effected under perfusion.

According to an aspect of some embodiments of the invention, the culturing of the adherent cells is effected for at least 3 days.

According to an aspect of some embodiments of the invention, the culturing of the adherent cells is effected until at least 10% of said adherent cells are proliferating.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5A shows the results from four different experiments while FIG. 5B shows the average of results obtained in FIG. 5A including standard deviation.

FIGS. 6A-C are bar graphs showing the effect of conditioned media of adherent cells from various placenta portions on endothelial cell proliferation. FIG. 6A shows proliferation of endothelial cells in conditioned media obtained from chorionic villi compared to non-conditioned medium and standard growth medium. FIG. 6B shows proliferation of endothelial cells in conditioned media obtained from decidua compared to non-conditioned medium and standard growth medium. FIG. 6C shows proliferation of endothelial cells in conditioned media obtained from amnion compared to non-conditioned medium and standard growth medium.

FIG. 8A depicts the paw pressure threshold as a function of time in the inflamed paw. FIG. 8B shows the same information for the contralateral paw.

DESCRIPTION OF EMBODIMENTS OF THE INVENTION

The present invention, in some embodiments thereof, relates to adherent cells from placenta and use of same in disease treatment.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Placenta represents a readily available source of cells endowed with unique immunosuppressive and tissue regeneration properties. Purified populations of adherent cells from the placenta or conditioned from those cells are valuable in treating conditions which can benefit from cell or organ transplantation.

In addition, the present inventor has devised a method for isolating highly purified cell populations from different portions of placenta (see Examples section below). Surprisingly it was uncovered that isolated cell populations from maternal portions of the placenta are characterized by unique morphological and functional properties which are distinct of other cell populations isolated from fetal placental fractions (see Examples section which follows). These cells are valuable for the treatment of a myriad of medical conditions.

Thus, according to an aspect of the present invention there is provided a population of adherent cells comprising at least about 70%, 75%, 80%, 85%, 90%, 92%, 94%, 95%, 96%, 98%, 99% or even 100% of cells from a maternal portion of placenta.

According to another aspect of the invention there is provided a population of cells comprising at least about 70%, 75%, 80%, 85%, 90%, 92%, 94%, 95%, 96%, 98%, 99% or even 100% adherent cells from a fetal portion of placenta.

According to specific embodiments the fetal portion of the placenta comprises amnion.

According to specific embodiments the fetal portion of the placenta consists of amnion.

According to specific embodiments the fetal portion of the placenta comprises chorionic villi.

According to specific embodiments the fetal portion of the placenta consists of chorionic villi.

As used herein the term "placenta" refers to the mammalian organ that connects the developing fetus to the uterine wall. Following birth, the placenta is expelled (and is referred to as a post partum placenta).

The placenta is preferably perfused for a period of time sufficient to remove residual cells (e.g., blood).

Figure 1:
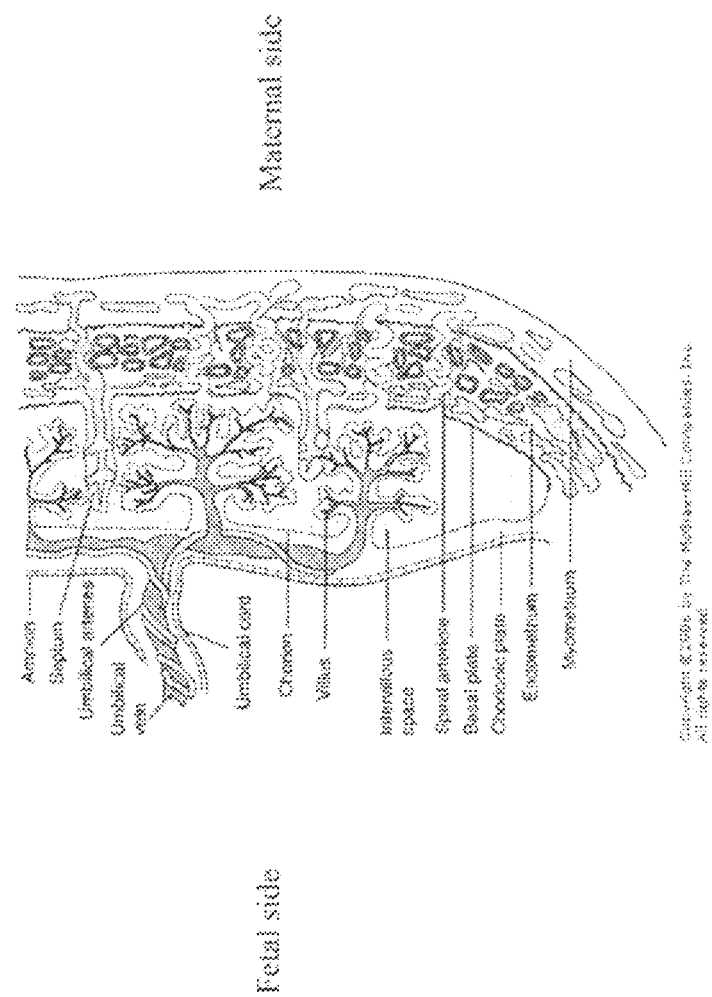
FIG. 1 is a schematic illustration of placenta structure and portions.

As used herein "fetal portion of placenta" refers to any portion of the placenta which is not maternal (see FIG. 1 for structural illustration).

As used herein "maternal portion of placenta" refers to any portion of the placenta which is not fetal (see FIG. 1 for structural illustration) e.g., those portions of the placenta which are derived from the decidua basalis or decidua parietalis.

Fetal portions of placenta include the amnion, chorion, or chorionic villi, see FIG. 1.

Methods of dissecting placenta to obtain cells are well known in the art. Some are described in details in the Examples section which follows.

Tissue specimens are washed in a physiological buffer [e.g., phosphate-buffered saline (PBS) or Hank's buffer]. Single-cell suspensions are made by treating the tissue with a digestive enzyme (see below) or/and mincing and flushing the tissue parts through a nylon filter or by gentle pipetting (Falcon, Becton, Dickinson, San Jose, Calif.) with washing medium.

Isolated adherent cells from the various portions of placenta may be derived by treating the tissue with a digestive enzyme such as collagenase, trypsin and/or dispase; and/or effective concentrations of hyaluronidase or DNAse; and ethylenediaminetetra-acetic acid (EDTA); at temperatures between 25-50° C., for periods of between 10 minutes to 3 hours. The cells may then be passed through a nylon or cheesecloth mesh filter of between 20 microns to 1 mm. Cells are centrifuged at speeds of between 100 to 3000×g for periods of between 1 minutes to 1 hour at temperatures of between 4-50° C. (see U.S. Pat. No. 7,078,230).

Cell retrieval is preferably effected under aseptic conditions. Once isolated cells are obtained, they are allowed to adhere to an adherent material (e.g., configured as a surface) to thereby isolate adherent cells.

As used herein the phrase "adherent cells" refers to cells which are anchorage dependent, i.e., require attachment to a surface in order to grow in vitro.

As used herein "an adherent material" refers to a synthetic, naturally occurring or a combination of same of a non-cytotoxic (i.e., biologically compatible) material having a chemical structure (e.g., charged surface exposed groups) which may retain the cells on a surface.

Examples of adherent materials which may be used in accordance with this aspect of the invention include, but are not limited to, a polyester, a polypropylene, a polyalkylene, a polyfluorochloroethylene, a polyvinyl chloride, a polystyrene, a polysulfone, a cellulose acetate, a glass fiber, a ceramic particle, a matrigel, an extra cellular matrix component (e.g., fibronectin, vitronectin, chondronectin, laminin), a collagen, a poly L lactic acid, a dextran and an inert metal fiber.

Further steps of purification or enrichment for adherent cells may be effected using methods which are well known in the art (such as by FACS using marker expression, as further described herein below).

Non-limiting examples of base media useful in culturing according to the invention include Minimum Essential Medium Eagle, ADC-1, LPM (Bovine Serum Albumin-free), F10(HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the invention is DMEM. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62 72, edited by William B. Jakoby and Ira H. Pastan, published by Academic Press, Inc.

The medium may be supplemented such as with serum such as fetal serum of bovine or human or other species, and optionally or alternatively, growth factors, vitamins (e.g. ascorbic acid), cytokines, salts (e.g. B-glycerophosphate), steroids (e.g. dexamethasone) and hormones e.g., growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor, fibroblast growth factor, nerve growth factor, cilary neurotrophic factor, platelet derived growth factor, and bone morphogenetic protein at concentrations of between picogram/ml to milligram/ml levels.

It is further recognized that additional components may be added to the culture medium. Such components may be antibiotics, antimycotics, albumin, amino acids, and other components known to the art for the culture of cells.

Further qualification of the cell populations, i.e., maternal or fetal placental cells, can be effected at each step of the purification process. For example, placenta of male embryos can be qualified for fetal or maternal cells based on karyotype analysis (i.e., XX cells are maternal while XY cells are fetal, see Examples section which follows).

Once obtained, adherent cells from the placenta can be used as is or propagated in culture. The cells may be passaged to 2D or 3D conditions. It will be appreciated though, that the cells may be transferred to a 3D-configured matrix immediately after isolation or alternatively, may be passaged to 3D settings following 2D conditions.

As used herein the phrase "two dimensional culture" refers to a culture in which the cells are disposed to conditions which are compatible with cell growth while allowing the cells to grow in one plane. The conditions in the two dimensional culture of the invention are designed to enable expansion of the adherent cells.

As used herein the phrase "three dimensional culture" refers to a culture in which the cells are disposed to conditions which are compatible with cell growth including a scaffold which allows cell to cell contacts in three dimensions. It is well appreciated that the in situ environment of a cell in a living organism (or a tissue) is in a three dimensional architecture. Cells are surrounded by other cells. They are held in a complex network of extra cellular matrix nanoscale fibers that allows the establishment of various local microenvironments. Their extra cellular ligands mediate not only the attachment to the basal membrane but also access to a variety of vascular and lymphatic vessels. Oxygen, hormones and nutrients are ferried to cells and waste products are carried away. The conditions in the three dimensional culture of the invention are designed to mimic such an environment as is further exemplified below.

It will be appreciated that the conditions of the two or three-dimensional culture are such that enable expansion of the adherent cells.

As used herein the terms "expanding" and "expansion" refer to substantially differentiation-less maintenance of the cells and ultimately cell growth, i.e., increase of a cell population (e.g., at least 2 fold) without differentiation accompanying such increase.

As used herein the terms "maintaining" and "maintenance" refer to substantially differentiation-less cell renewal, i.e., substantially stationary cell population without differentiation accompanying such stationarity.

For 2D culturing, seeding of placenta cells is typically effected at a culture density of $3\pm0.2\times10^3$ cells/cm$^2$. Following seeding, cell cultures are usually cultured in a tissue culture incubator under humidified conditions with 5% $CO_2$ at 37° C.

According to an embodiment of the present invention, the cells are grown in a culture medium devoid of antibiotic supplements from at least passage 2, at least passage 3, or at least passage 4.

According to an embodiment of the present invention, the cells are passaged for at least 4 passages, at least 5 passages, at least 6 passages, at least 7 passages or at least 8 passages. It will be appreciated that cells are typically passaged when the culture reaches about 70-90% confluence, typically after 3-5 days (e.g., 1-3 doublings).

For 3D culturing, adherent cells may be transferred to a 3D-configured matrix immediately after isolation or alternatively, may be passaged to three dimensional settings following two dimensional (2D) conditions. At times, cryopreservation of cells between the 2D culture and the 3D culture may be needed.

Thus, the adherent material according to some embodiments is configured for 3D culturing thereby providing a growth matrix that substantially increases the available attachment surface for the adherence of the cells so as to mimic the infrastructure of the tissue (i.e., placenta).

For high scale production, culturing can be effected in a 3D bioreactor.

Examples of such bioreactors include, but are not limited to, a plug flow bioreactor, a continuous stirred tank bioreactor, a stationary-bed bioreactor (packed bed bioreactor) and a fluidized bed bioreactor.

The Celligen bioreactor (New Brunswick Scientific) is capable of 3D expansion of adherent cells under controlled conditions (e.g. pH, temperature and oxygen levels) and with constant cell growth medium perfusion. Furthermore, the cell cultures can be monitored for concentration levels of glucose, lactate, glutamine, glutamate and ammonium. The glucose consumption rate and the lactate formation rate of the adherent cells enable one to measure cell growth rate and to determine the harvest time.

Other 3D bioreactors that can be used with the invention include, but are not limited to, a continuous stirred tank bioreactor, where a culture medium is continuously fed into the bioreactor and the used medium is continuously drawn out, to maintain a time-constant steady state within the bioreactor. The stirred tank bioreactor may be used with fluidized bed (suspended carriers) or a fibrous bed basket (which is available for example at New Brunswick Scientific Co., Edison, N.J.), a stationary-bed bioreactor, an air-lift bioreactor, where air is typically fed into the bottom of a central draught tube flowing up while forming bubbles, and disengaging exhaust gas at the top of the column, a bioreactor with Polyactive foams [as described in Wendt, D. et al., Biotechnol Bioeng 84: 205-214, (2003)], a porous scaffolds in a Radial-flow perfusion bioreactor [as described in Kitagawa et al., Biotechnology and Bioengineering 93(5): 947-954 (2006)], a radial flow bioreactor with scaffold or carriers, a hollow fiber bioreactor, and micro carriers. Other bioreactors which can be used in accordance with the invention are described in U.S. Pat. Nos. 6,277,151, 6,197,575, 6,139,578, 6,132,463, 5,902,741 and 5,629,186.

In an exemplary embodiment a total of $200\pm100\times10^6$ cells are seeded, $3\text{-}10\times10^6$ cell/gr carrier are seeded, or $0.06\text{-}0.2\times10^6$ cell/ml are seeded. According to an exemplary embodiment, cell seeding is effected at 2000-9000 cells/cm2 FibraCel disks.

Cells can be harvested when at least about 10% of cells are proliferating while avoiding uncontrolled differentiation and senescence.

Culturing is effected for at least about 2 days, 3 days, 4 days, 5 days, 6 days, 7 days, 10 days, 14 days, 20 days, a month or even more. It will be appreciated that culturing in a bioreactor may prolong this period. Culturing of the adherent cells in the 3D culture can be effected under a continuous flow of a culture medium. Passaging may also be effected to increase cell number. It will be appreciated that culture medium may be changed in order to prolong and improve culturing conditions.

According to an embodiment of the present invention, the cell culturing is effected under perfusion of the culture medium. Typically, the perfusion rate is determined by the glucose concentration in the culture medium of the adherent cells. Thus, according to the present teachings, the culture medium may be changed when the glucose concentration is about 500 mg/L, about 550 mg/L, or about 600 mg/L.

Adherent cells of some embodiments of the present invention comprise at least about 10%, 28%, 30%, 50%, 80% or more proliferative cells (as can be assayed by FACS monitoring S and G2/M phases).

Adherent cells of some embodiments of the invention may comprise at least one "stromal cell phenotype".

As used herein "a stromal cell phenotype" refers to a structural or functional phenotype typical of a bone-marrow derived stromal (i.e., mesenchymal) cell.

Thus for example, the cells may have a spindle shape. Alternatively or additionally the cells may express a marker or a collection of markers (e.g. surface marker) typical to stromal cells. Examples of stromal cell surface markers (positive and negative) include but are not limited to $CD105^+$, $CD29^+$, $CD44^+$, $CD73^+$, $CD90^+$, $D7\text{-fib}^+$, $CD3^-$, $CD4^-$, $CD34^-$, $CD45^-$, $CD80^-$, $CD5^-$, $CD20^-$, $CD11b^-$, $CD14^-$, $CD19^-$, $CD79^-$, $HLA\text{-}DR^-$, $CD31^-$, $KDR^-$, and $FMC7^-$.

Other stromal cell markers include but are not limited to tyrosine hydroxylase, nestin and H—NF.

According to a specific embodiment of the invention, adherent cells, including those derived from either a maternal portion or a fetal portion of the placenta, do not express the stem cell marker CD271.

As used herein the phrase "stem cell" refers to a cell which is not terminally differentiated.

According to a specific embodiment of the invention, adherent cells derived from a fetal portion of the placenta (e.g., consisting of or comprising chorionic villi) are characterized by a positive CD200 expression (see Examples section which follows).

According to a specific embodiment of the invention, not more than 3.5%, not more than 3%, not more than 2%, or not more than 1% of the adherent cells from a maternal portion express CD200 as measured by flow cytometry using an isotype control to define negative expression.

Examples of functional phenotypes typical of stromal cells include, but are not limited to, T cell suppression activity (they don't stimulate T cells and conversely suppress same, for example, when tested in a mixed lymphocyte culture) and hematopoietic stem cell support activity.

According to an exemplary embodiment, the adherent cells of the present invention are less committed to differentiation into osteogenic or adipogenic lineages as compared to adherent cells from the bone marrow grown and differentiated under the same conditions. For example, according to an exemplary embodiment, the adherent cells of the present invention do not differentiate into osteogenic or adipogenic lineages when grown under the conditions described in Examples 4-7 of WO2010026575, which is incorporated by reference in its entirety.

According to one embodiment of the invention, the adherent cells of the invention are capable of suppressing immune reaction in a subject.

As used herein the phrase "suppressing immune reaction in a subject" refers to decreasing or inhibiting the immune reaction occurring in a subject in response to an antigen (e.g., a foreign cell or a portion thereof). The immune response which can be suppressed by the adherent cells include the humoral immune responses, and cellular immune responses, which involve specific recognition of pathogen antigens via antibodies and T-lymphocytes (proliferation of T cells), respectively. Some examples of methods of determining whether the adherent cells suppress an immune reaction are given in the Examples.

According to a specific embodiment, adherent cells of maternal placenta are capable of suppressing an immune reaction to a lesser extend (e.g., at least about 2% less, 5% less, 10% less, 15% less, 20% less, 30% less, 40% less or 50% less) than adherent cells from a fetal portion of placenta. In some embodiments, suppression of an immune reaction is determined by measuring the ability of the cells to suppress a mixed lymphocyte culture. In other embodiments, suppression of an immune reaction is determined by measuring suppression of T cell blast formation induced by phytohemaglutenin (PHA) in an in vitro assay.

According to a specific embodiment, adherent cells of maternal placenta comprise a cell diameter which is smaller (e.g., by about 2%, 5%, 10%, 15%, 20 or 30%) than that of adherent cells derived from a fetal portion of placenta.

According to a specific embodiment, adherent cells of maternal placenta comprise a cell proliferation capacity (e.g., by about 2%, 5%, 10%, 15%, 20% or 30%) which is higher than that of adherent cells derived from a fetal portion of placenta.

According to a specific embodiment the cells can be of autologous, syngeneic, allogeneic or xenogeneic source.

According to another specific embodiment the cells can be genetically modified to express a heterologous protein.

According to yet another specific embodiment the cells are not genetically modified.

It will be appreciated that conditioned medium can be isolated from cultures comprising/consisting of the cells.

As used herein "conditioned medium" refers to a medium enriched with secreted factors present in the cultures described herein (i.e., comprising/consisting of any of the above cell populations) following a certain culturing period.

The conditioned medium is produced by culturing the above cells in a growth medium under conditions suitable for producing the conditioned medium.

The growth medium may be any growth medium suitable for growing the adherent placenta cells of the present invention, as described hereinabove. The growth medium may be supplemented with nutritional factors, such as amino acids, (e.g., L-glutamine), anti-oxidants (e.g., beta-mercaptoethanol) and growth factors. Serum and/or serum replacements are added at effective concentration ranges of up to 20%.

Cells are cultured in the growth medium for sufficient time to allow adequate accumulation of secreted factors to support immunosuppression and/or angiogenesis for example. Typically, the medium is conditioned by culturing for 1-5 days at 37° C. However, the culturing period can be scaled by assessing the effect of the conditioned medium on immunosuppression and/or angiogenesis e.g., as described in the Examples. In some embodiments, the medium is conditioned for 3-5 days for immunosuppression and for 24-72 hrs for angiogenesis.

Selection of culture apparatus for conditioning the medium is based on the scale and purpose of the conditioned medium. Large scale production preferably involves the use of bioreactors as described hereinabove. Following accumulation of adequate factors in the medium, growth medium (i.e., conditioned medium) is separated from the cells and collected. It will be appreciated that the cells can be used repeatedly to condition further batches of medium over additional culture periods, provided that the cells retain their ability to condition the medium.

The conditioned medium of the present invention may be administered directly (as further described below) or extracted to concentrate the effective factor such as by salt filtration. For future use, conditioned medium is preferably stored frozen at −80° C.

Adherent cells of fetal portions can be used in various research settings such as for testing their biological properties (e.g., morphology, size) with respect to maternal portions (see e.g., Examples section).

The purified populations of cells from the placenta described herein or any of the conditioned media described herein can be used for treating a condition which can benefit from cell or organ transplantation.

As used herein, the term "condition" refers to any pathology (disease, condition, syndrome or disorder) which may benefit from cell (e.g. stromal cell) or organ transplantation. Examples include ischemic conditions, cardiovascular conditions, nervous system conditions, gastrointestinal tract conditions, orthopedic conditions, hematopoietic conditions, renal conditions and hepatic conditions, such as but are not limited to, peripheral arterial disease (PAD), such as limb ischemia and critical limb ischemia (CLI), lower extremity ischemia, ischemic vascular disease, stroke, ischemic heart disease, myocardial ischemia, acute myocardial infarction (MI), coronary artery disease (CAD), atherosclerotic cardiovascular disease, left main coronary artery disease, arterial occlusive disease, peripheral ischemia, peripheral vascular disease, arteriosclerosis, retinopathy, retinal repair, remodeling disorder, von Hippel-Lindau syndrome, hereditary hemorrhagic telengiectasiaischemic vascular disease, Buerger's disease, diabetes, vascular disease of the kidney, ischemic renal disease, liver disease, ischemic placenta, reproduction associated disorders, graft-versus-host disease (GVHD), solid organ transplant, hematopoietic stem cell transplantation (HSCT), inflammatory conditions of the gastrointestinal (GI) tract, ulcerative colitis, delayed wound-healing, delayed ulcer healing, cancer (e.g. breast cancer), pre-cancer, conditions characterized by connective tissue damage such as bone cancer, osteosarcoma, bone metastases, bone fracture, degenerative disc disease, osteogenesis imperfecta (OI), burn, burn wound, articular cartilage defect, deep wound, delayed wound-healing, delayed ulcer healing, metabolic disorders, psoriasis, neuropathic pain, peripheral nerve injury, support of kidney transplantation, subchondral-bone cyst, osteoporosis, osteoarthritis (OA), degenerated bone, cartilage damage, articular cartilage defect, injured tendons (e.g. overstrain-induced injuries of tendons) and injured ligaments.

Ischemic disease/condition is a medical condition in which tissue falls into an ischemic state due to a reduced blood flow in the vasculature caused by various factors, such as constriction of the vessel lumen, development of blood clots, vessel occlusion, vasculitis, vessel shrinkage, or an increase in blood viscosity. Ischemic diseases include peripheral vascular disorder, ischemic heart disease (e.g., ischemic cardiomyopathy, myocardial infarction, ischemic heart failure), ischemic cerebrovascular disease, including stroke, ischemic kidney disease, ischemic lung disease, and ischemic diseases associated with infectious diseases. Additional non-limiting examples of ischemic diseases (also referred to herein as ischemia) are listed throughout the application.

Peripheral vascular disorder is a medical condition in which peripheral tissue falls into an ischemic state due to a reduced peripheral arterial blood flow caused by, for example, constriction of the vessel lumen, development of blood clots, vessel occlusion, vasculitis, vessel shrinkage, or an increase in blood viscosity. Diseases associated with peripheral vascular disorder include chronic arterial occlusive diseases such as arteriosclerosis obliterans and Buerger's disease, and progressive systemic sclerosis, systemic erythematosus, Raynaud's disease, vibration syndrome, aneurysm, and vasculitis. Additional non-limiting examples of peripheral ischemic diseases are listed throughout the application.

According to a specific embodiment the condition is heart failure, myocardial infarction, neuropathic pain, skeletal muscle defect and ischemic heart disease.

According to a specific embodiment, the conditioned medium described herein is used for treating stroke.

As used herein "stroke" or "acute cerebrovascular attack" refers the rapidly developing loss of brain function(s) due to disturbance in the blood supply to the brain. This can be due to ischemia (lack of glucose and oxygen supply) caused by thrombosis or embolism or due to a hemorrhage (subarachnoid hemorrhage or intracerebral hemorrhage).

It will be appreciated that the cells of the present invention are capable of inducing immunosuppression and/or tolerance and/or are capable of inducing angiogenesis in a subject. Thus, the adherent cells or conditioned media derived therefrom may be used to treat any condition in need of angiogenesis and/or immunosuppression and/or tolerance. Such conditions included, but are not limited to, autoimmune diseases and inflammatory diseases (including acute and chronic inflammatory diseases) including, but not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et at, Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M.

Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Furthermore, the adherent cells or conditioned media may be used to treat diseases associated with transplantation of a graft including, but are not limited to, graft rejection, chronic graft rejection, subacute graft rejection, hyperacute graft rejection, acute graft rejection and graft versus host disease.

As used herein the term "treating" refers to inhibiting or arresting the development of a pathology and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology. The term "treating" may also refer to alleviating or diminishing a symptom associated with the pathology.

The subject treated by the adherent cells or conditioned media may be any subject (e.g., a mammal), such as a human subject or a domesticated animal including, but not limited to, horses (i.e. equine), cattle, goat, sheep, pig, dog, cat, camel, alpaca, llama and yak who is diagnosed with or suffers from the pathology and can benefit from stromal cell transplantation.

As mentioned cells may be naïve or may be genetically modified such as to derive a lineage of interest (see U.S. Pat. Appl. No. 20030219423).

The cells may be of fresh or frozen (e.g., cryo-preserved) preparations.

Depending on the medical condition, the subject may be administered with additional chemical drugs (e.g., immunomodulatory, chemotherapy etc.) or cells.

The cells, though characterized by immuno-suppressive activity, may still provoke host or donor-derived undesirable immune response. Approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylidene-acetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

Furthermore, it will be appreciated that the cells or conditioned media can be administered either per se or, preferably as a part of a pharmaceutical composition that further comprises a pharmaceutically acceptable carrier.

As used herein a "pharmaceutical composition" refers to a preparation of the cells or conditioned media derived therefrom, with other chemical components such as pharmaceutically suitable carriers or excipients. The purpose of a pharmaceutical composition is to facilitate administration of the cells to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, DMSO, HSA, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Pharmaceutical compositions for use in accordance with the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, physiological salt buffer, or freezing medium containing cryopreservents.

Determination of a therapeutically effective amount is well within the capability of those skilled in the art, especially in light of the detailed disclosure provided herein.

Toxicity and therapeutic efficacy of the active ingredients described herein can be determined by standard pharmaceutical procedures in vitro, in cell cultures or experimental animals.

Depending on the severity and responsiveness of the condition to be treated, dosing can be of a single or a plurality of administrations. However, the amount of a composition to be administered will, of course, be dependent on the subject being treated, the severity of the affliction, the manner of administration, the judgment of the prescribing physician, etc.

Following transplantation, a portion of the cells of the invention preferably survive in the diseased area for a period of time (e.g. about 2-6 weeks), such that a therapeutic effect is observed.

Compositions including the preparation of the invention formulated in a compatible pharmaceutical carrier may also be prepared, placed in an appropriate container, and labeled for treatment of an indicated condition.

Compositions of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

As used herein the term "about" refers to ±10%.

The terms "comprises," "comprising," "includes," "including," "having" and their conjugates mean "including but not limited to." This term encompasses the terms "consisting of" and "consisting essentially of."

The phrase "consisting essentially of" means that the composition or method may include additional ingredients and/or steps, but only if the additional ingredients and/or steps do not materially alter the basic and novel characteristics of the claimed composition or method.

As used herein, the singular form "a," "an," and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a Condition, substantially ameliorating clinical or aesthetical symptoms of a condition or substantially preventing the appearance of clinical or aesthetical symptoms of a condition.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Recovery and Processing of Adherent Cells from Placenta

Isolation of Adherent Stromal Cells (ASC's)—Term human placentas were derived following caesarean sections from healthy donor mothers following informed consent.

The minced tissue from the placenta was incubated for 2-5 hours at 37° C. with 0.1% Collagenase (1 mg Collagenase/ml tissue). Two dimensional (2D) cell medium (2D-Medium comprising DMEM supplemented with 10% FBS, fungizone 0.25 µg/ml and Gentamycine 50 µg/ml) was added and the digested tissue was roughly filtered through a sterile metal strainer, collected in a sterile beaker and centrifuged (10 minutes, 1200 RPM, 4° C.). Using gentle pipetting, suspended cells were then diluted with 2D-Medium supplemented with antibiotics, seeded in 175 cm$^2$ flasks and incubated at 37° C. in a tissue culture incubator under humidified conditions supplemented with 5% $CO_2$. Following 2-3 days, in which the cells were allowed to adhere to the flask surface, they were washed with PBS and 2D-Medium was added.

Two Dimensional (2D) Cell Growth—The first passage was typically carried out after 7-15 days. Beginning at passage 2 and continuing until passage 6-8, cells were passaged when the culture reached 70-90% confluence, usually after 4-5 days (1.5-2 doublings). The cells were detached from the flasks using 0.25% trypsin-EDTA (4 minutes at 37° C.) and seeded in a culture density of $4\pm0.5\times10^3$ cells/cm$^2$. Throughout the process, cultures were grown in a tissue culture incubator under humidified conditions with 5% CO2 at 37° C. After a total of 5-9 passages cells were collected and cryopreserved.

Cryopreservation Procedure for 2D-Cell-Stock Product— For 2D cell stock cryopreservation, 2D-cultured cells were collected under aseptic conditions using 0.25% trypsin-EDTA. The cells were centrifuged (1200 RPM, 10', 4° C.), counted and resuspended in 2D-Medium.

For freezing, cell suspensions were diluted 1:1 with 2D-Freezing Mixture (final concentrations was 10% DMSO, 40% FBS and 50% 2D-Medium). Cells were stored at a final concentration of $10\times10^6$/ml in 5 ml cryopreservation polypropylene vials. The vials were labeled and transferred to a controlled rate freezer for a graduated temperature reducing process (1° C./min), after which they were transferred to storage in gas-phase of a liquid nitrogen freezer.

Further details concerning the isolation and culture of placental ASC's under 2D and 3D conditions are found in the following references. WO2007/108003, which is incorporated by reference in its entirety, describes three dimensional (3D) culturing conditions suitable for expansion of placental derived ASC's. WO2009/037690, which is incorporated by reference in its entirety, teaches methods of treating ischemia and inducing connective tissue regeneration by administering to the subject a therapeutically effective amount of adherent cells of a tissue selected from the group consisting of a placenta and an adipose tissue. WO2010/026574, which is incorporated by reference in its entirety, describes two dimensional (2D) culturing conditions suitable for expansion of placental derived ASC's. WO2010/026575, which is incorporated by reference in its entirety, describes three dimensional (3D) culturing conditions involving perfusion that are suitable for expansion of placental derived ASC's.

origin are necessarily XX (female karyotype) while cells of fetal origin are necessarily XY (male karyotype). Results are summarized in Table 1, below.

TABLE 1

| Batch no. | Passage Number | Cell Source | Karyotype | | Cell Source | | | Cell Source | | |
|---|---|---|---|---|---|---|---|---|---|---|
| | | | FISH test | | | FISH test | | | FISH test | |
| | | | XX | XY | | XX | XY | | XX | XY |
| P070109 | 4-5 | Decidua | 70% | 30% | Villus | 0% | 100% | Amnion | 20% | 81% |
| P190109 | 5 | | 99% | 1% | | 0% | 100% | | 1% | 99% |
| P150609 | 5 | | 96% | 4% | | 0% | 100% | | 10% | 90% |
| P290609 | 5 | | 99% | 1% | | 8% | 92% | | 0% | 100% |
| P050809 | 5 | | 98% | 2% | | 27% | 74% | | 1% | 99% |

Results clearly demonstrate that Decidua derived cells are enriched for maternal (XX) cells, while the villus and amniotic membrane derived cells are enriched for Fetal (XY) cells.

II. Characterization of Adherent Cells from Different Placental Portions

Cell Morphology

Figure 2:
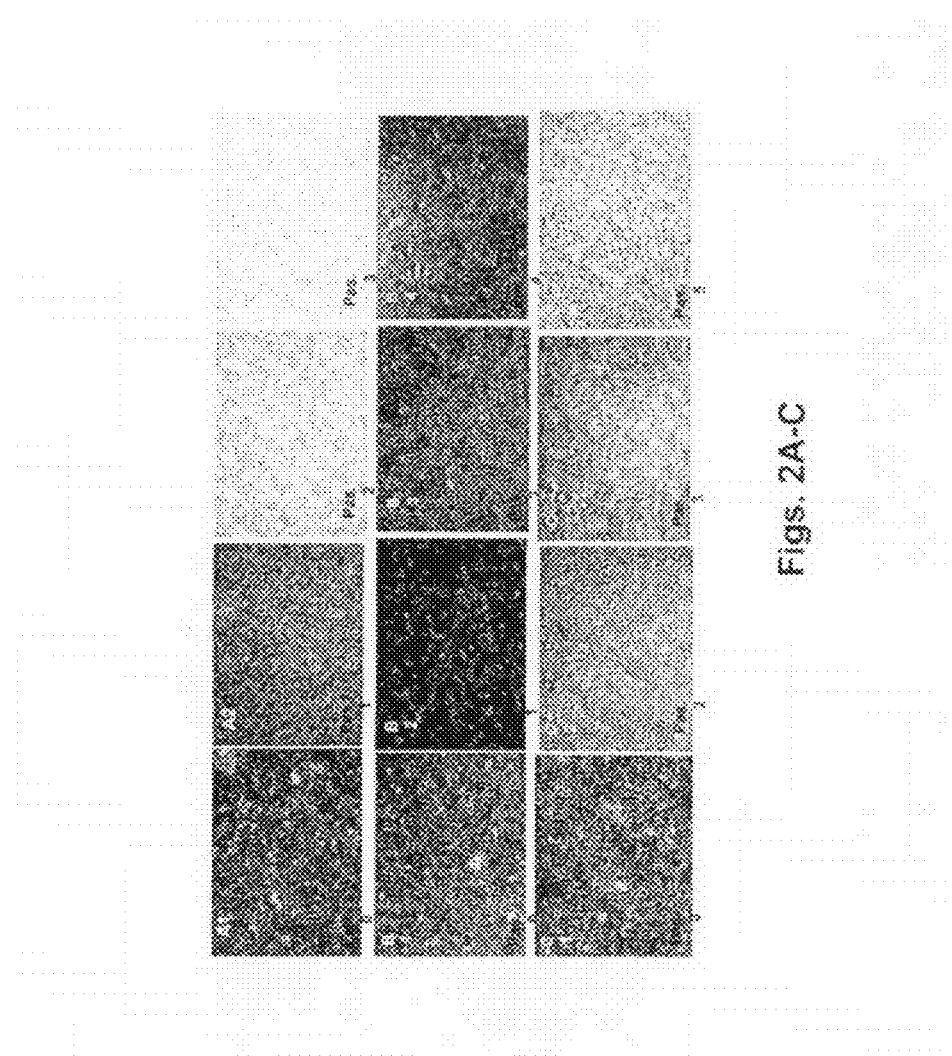
FIG. 2A-C are photomicrographs showing the morphology of adherent cells derived from placenta decidua basalis (A), villous stroma (B), and amniotic membrane (C).

The morphology and size (in diameter) of the cells obtained from the different Placenta regions as described above was examined during cell expansion. Cells were cultured in DMEM (low glucose) including 8% FBS and passaged for five to seven population doublings. FIGS. 2A-C show the morphology of cells derived from placenta decidua basalis, chorionic villus, and amniotic membrane. Phase contrast at magnification ×40 was used for all figures. (A): The morphology of adherent cells derived from placenta decidua basalis. (1):8 days after isolation (passage 0), (2):13 days after isolation (passage 1), (3): 20 days after isolation (passage 2), (4):24 days after isolation (passage 3). (B): The morphology of adherent cells derived from placenta villous stroma. (1):13 days after isolation (passage 0), (2):17 days after isolation (passage 1), (3): 22 days after isolation (passage 2), (4):31 days after isolation (passage 4). (C): The morphology of adherent cells derived from placenta amniotic membrane. (1):3 days after isolation (passage 0), (2):20 days after isolation (passage 2), (3): 29 days after isolation (passage 3), (4):41 days after isolation (passage 5). The phase micrographs showed difference in the morphology of cells derived from Decidua basalis, Chorionic villus and Amniotic membrane of human term placenta. These results are in accordance with the cell diameter measurements (as described below).

Example 2

Isolation and Characterization of Placental Fractions

I. Isolation of Adherent Cells from Different Placental Portions

Materials and Methods

Placenta—Term human placentas were derived following caesarean sections of male fetuses from healthy donor mothers following informed consent.

Cell isolation (for structural illustration see FIG. 1)

Cell isolation from Amniotic membrane—Placenta was placed with the fetal side facing up. The amniotic membrane (avascular) was separated from the chorion membrane by blunt mechanic peeling. The amniotic membrane was transferred to a 50 ml tube containing Hank's balanced salts solutions (HBSS). The membrane was cut into pieces of ~0.5-1 cm$^2$ and placed in a new 50 ml tube.

Cell isolation from the Decidua part—This step was performed following removal of the amniotic membrane as detailed above. The placenta was placed with maternal side facing up. The decidua was dissected only from the central region of the maternal-facing surface (see FIG. 1). Squares of ~1 cm$^3$ were cut in depth of not more than 0.5 cm. The pieces were placed in a 500 ml bottle containing HBSS and washed with HBSS.

Cell isolation from the Chorionic villus part—This step was performed following removal of the Decidua part as detailed above. The placenta was re-placed with the fetal side faced up. Squares of ~4-5 cm$^3$ were cut between the big blood vessels in depth of ~0.5-1 cm. Each piece was placed on a sterile glass plate and scrubbed using a scalpel. The Villus (small blood vessels) were separated and only the surrounding tissue was collected without the chorine amniotic membrane layer. The minced tissue was placed in 500 ml bottle containing HBSS and washed with HBSS.

Isolation of adherent cells—The minced tissue of the various placenta regions obtained as described above was processed as described for the preparation of PLX cells above.

Figure 3:
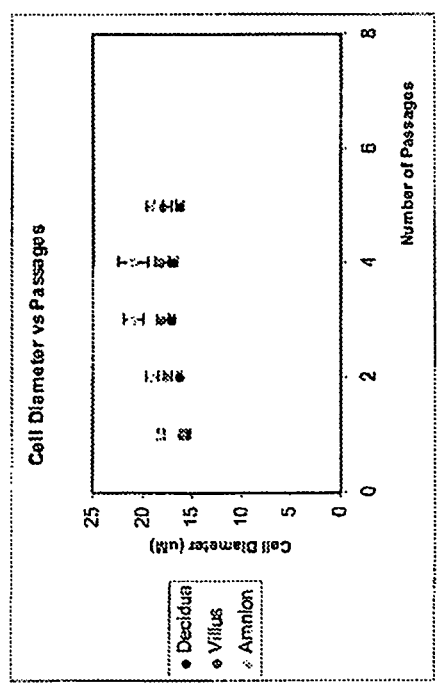
FIG. 3 is a graph showing cell diameter versus number of passages of cells from different placental portions.

Determination of cell origin—In order to determine whether the cells obtained from the various placenta regions following the isolation and expansion conditions as described above are of maternal or fetal origin, a FISH analysis was performed on cells derived according to this protocol from 5 placentas obtained from male newborns. Cells of maternal Cell Size Cell size (in diameter) of the cells originating from the three different placenta portions was measured at each passage using the Cedex automated cell analyzer (Roche Innovatis AG). Results are presented as cell diameter versus number of passages: FIG. 3 shows the average cell diameter of all tested batches between passages 2-5.

Results show a significant difference in cell diameter per passage between decidua, villus and amniotic membrane. Cell size of cells originating from decidua, villus and amniotic membrane was 15.5-17, 16.0-18.1 and 18.1-21 respectively.

Population Doubling Rate of the Cells

At each passage cells were counted and population doubling rate per day was calculated according to equation 1:

$$\text{Log(total viable cells at harvest/total viable cells at seed)/days of culture} \qquad \text{Equation 1}$$

Figure 4:
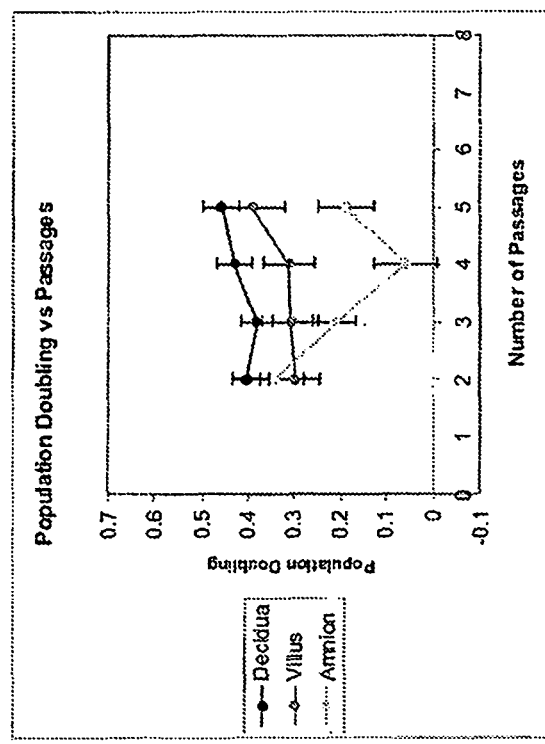
FIG. 4 is a graph showing population doubling versus number of passages of cells from different placental portions.

The average PD rate of cells derived from the Decidua, Amniotic membrane and Villus through passages 1 to 5 is presented in FIG. 4.

The proliferation rate of placenta Decidua basalis derived cells is significantly higher than placenta Chorionic villus and Amniotic membrane derived cells. Amniotic membrane cell proliferation slow dramatically between passages 2-4, while beyond passage 4 there is a tendency of improvement in cell proliferation Immunophenotype FRCS analysis of membrane markers—cells were stained with monoclonal antibodies. Briefly, 400,000-600,000 cells were suspended in 0.1 ml flow cytometer buffer in a 5 ml test tube and incubated for 15 minutes at room temperature (RT), in the dark, with each of the monoclonal antibodies presented in Table 2, below. Cells were washed twice with flow cytometer buffer, resuspended in 500 µl flow cytometer buffer and analyzed by flow cytometry using FC-500 Flow Cytometer (Beckman Coulter). Negative controls were prepared with isotype-matching fluorescence molecules.

TABLE 2

Antibodies

| Antibody | Fluorescence conjugate | Manufacturer | Catalog number |
|---|---|---|---|
| Anti human CD45 | FITC | IQ Products | IQP-124F |
| Anti human CD105 | PE | eBioscience | 12-1057-73 |
| Anti human CD 19 | PE | IQ Products | IQP-515R |
| Anti human CD14 | FITC | IQ Products | IQP-143R |
| Anti human CD29 | FITC | eBioscience | 11-0297 |
| Anti human CD73 | PE | BD Pharmigen | 550257 |
| Anti human CD90 | PE | BD Pharmigen | 555596 |
| Anti human CD200 | PE | BD Pharmigen | 552475 |

Table 3 below, outlines the results of marker expression.

TABLE 3

Marker expression on adherent cells from different cell sources

| Batch no | Cell Source | Passage Number | CD105 | CD90 | CD73 | CD29 | CD45 | CD19 | CD14 | CD200 |
|---|---|---|---|---|---|---|---|---|---|---|
| PO50809 | Villus | 5 | 98.1 | 95.1 | 95.7 | 98.6 | 0.0 | 0.4 | 0.3 | 57.9 |
|  | Decidua | 5 | 99.7 | 98.4 | 99.8 | 99.5 | 0.1 | 0.0 | 0.0 | 1.2 |
|  | Amnion | 5 | 85.1 | 92.9 | 79.9 | 89.1 | 0.0 | 0.1 | 0.1 | 0.0 |
| P190109 | Villus | 5 | 99.43 | 99.9 | 99.6 | 99.7 | 0.1 | 0.1 | 0.0 | 60 |
|  | Decidua | 5 | 99.65 | 99.4 | 99.5 | 99.4 | 0.0 | 0.0 | 0.0 | 0 |
|  | Amnion | 5 | 98.3 | 99.6 | 99.3 | 99.6 | 0.1 | 0.1 | 0.0 | 44.5 |
| P150609 | Villus | 5 | 92.43 | 86.9 | 92.1 | 97.5 | 19.7 | 0.0 | 0.0 | 16.8 |
|  | Decidua | 5 | 99.25 | 81.7 | 99.4 | 99.2 | 0.1 | 0.1 | 0.0 | 0.3 |
|  | Amnion | 5 | 88.02 | 94.9 | 96.7 | 94.9 | 0.0 | 0.0 | 0.0 | 31.6 |
| P290609 | Villus | 5 | 99.6 | 90.8 | 98.4 | 94.6 | 0.0 | 0.1 | 0.2 | 17.8 |
|  | Decidua | 5 | 99.5 | 94.4 | 99.3 | 97.9 | 0.0 | 0.0 | 0.1 | 1.1 |
|  | Amnion | 5 | 98.0 | 92.0 | 97.3 | 91.6 | 0.3 | 0.1 | 0.0 | 13.0 |
| PO70109 | Villus | 5 | 96.06 | 99.9 | 96.1 | 99.1 | 0.0 | 0.1 | 0.0 | 57.8 |
|  | Decidua | 5 | 99.24 | 99.3 | 98.7 | 99.4 | 0.2 | 0.0 | 0.0 | 3.5 |
|  | Amnion | 4 | 86.8 | 87.0 | 83.7 | 82.0 | 0.6 | 0.0 | 0.3 | 8.6 |

Of note, decidua derived cells showed very low expression of CD200 in comparison to cells derived from villus and amnion.

III. In Vitro Immunomodulation Properties of the Various Placenta Portions

Human derived mononuclear cells (MNCs) were isolated from peripheral blood. Suspension of 200,000 MNCs per 200 µl medium (RPMI 1640 medium containing 20 FBS per 96 well) were stimulated with 10 µg PHA/ml (SIGMA) in the presence of 40,000 cells originating from Decidua, Villus and amniotic membrane for 3 days under humidified 5% C02 at 37° C. Cells derived from four different placentas were used. Three replicates of each group were seeded in 96-well plates. During the last 18 hrs of the $3^{rd}$-day of culture, cells were pulsed with EdU (5-ethynyl-2'-deoxyuridine), to a final concentration of 10 µM.

Cell proliferation was analyzed using the Click It kit (Invitrogen) according to manual.

Figure 5A:
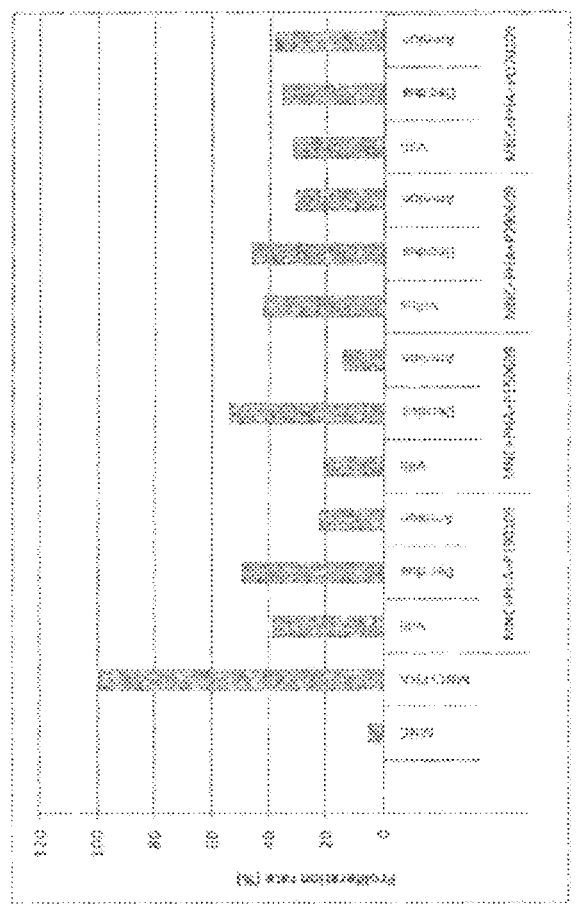
FIGS. 5A-B are histograms showing in vitro immunomodulation properties of the various placenta portions.

Results demonstrate (FIG. 5A) that all three cell populations derived from 4 different placentas inhibit the proliferation of PHA activated MNC.

Figure 5B:
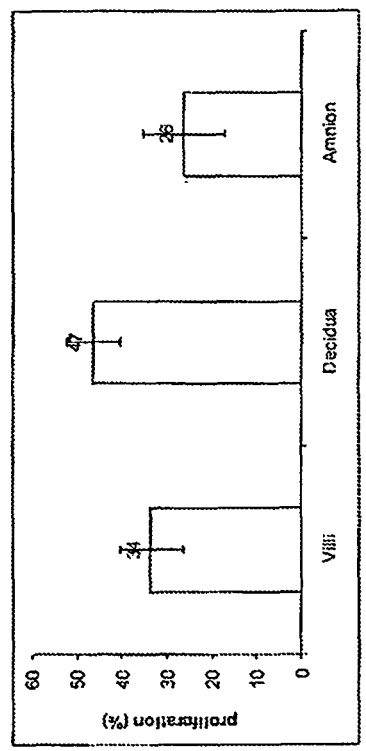

The average inhibition rate (FIG. 5B) suggests a stronger anti-proliferative effect of amniotic membrane and villus derived cells compared to decidua derived cells.

Example 3

In Vitro Angiogenic Properties of Conditioned Media Derived (CM) from the Various Placenta Portions Experimental Procedures Placenta cells of the various fractions were seeded in 6 wells plate (0.5×10$^6$/well) within 4 ml DMEM medium supplemented with 8% FCS for 24 hours.

After 24 hr, DMEM was removed, wells were washed gently with 1 ml PBS and replaced with 4 ml BIO-MPM (Biological industries) supplemented with Fungizone (0.25 µg/ml) Gentamicin-IKA (45 µg/ml) ECGS (1 mg/ml) Heparin (5 U/ml) and Glutamine (2 Mm) without serum. After 24 hrs CM was collected and centrifuged for 1 minute in 4600 RPM. CM was either used fresh or kept at −80° C. until use.

Placenta derived CM as described above was added to HUVEC (Human Umbilical Vein Endothelial Cells) prepared as follows:

15,000/cells per well were thawed and seeded on fibronectin coated 12 well plates with M-199 medium supplemented with 20% FCS for 24 hours. Medium was removed and replaced with a mixture of 50% fresh full BIO-MPM {supplemented with Fungizone (0.25 µg/ml) Gentamicin-IKA (45 µg/ml) ECGS (1 mg/ml) Heparin (5 U/ml) and Glutamine (2 Mm) supplemented with 10% FCS} and 50% of fresh or frozen placenta derived CM as described above.

HUVEC proliferation was assessed 72 hrs following addition of CM by the automated Cedex cell counter Results shown in FIGS. 6A-C clearly indicate that CM obtained from all three placenta portions induced an elevation in HUVEC proliferation in comparison to non-conditioned similar medium BIO-MPM+5% serum medium and even in comparison to M199+20% serum which is the standard growth medium utilized for HUVEC expansion.

Example 4

In Vivo Models for Testing Therapeutic Efficacy

I. Skeletal Muscle Regeneration

Insufficient post-traumatic skeletal muscle regeneration with consecutive functional efficiency continues to be a serious problem in orthopedic and trauma surgery. Multiple efforts have been undertaken to transfer techniques of tissue engineering to successfully improve muscle defect regeneration (Li and Huard 2002; Bach, Beier et al. 2004; Kamelger, Marksteiner et al. 2004; Peng and Huard 2004). Local application of myoblasts into a muscle defect enhances regeneration, resulting in an improvement of contraction force of approximately 40% (Arcila, Ameredes et al. 1997; Irintchev, Langer et al. 1997; Saxena, Marler et al. 1999; DeRosimo, Washabaugh et al. 2000). However, transfer of this approach into clinical routine is limited by donor site morbidity. Transplantation of autologous muscle precursor cells has shown encouraging results in muscle trauma treatment but is associated with significant donor site morbidity (Huard, Cao et al. 2003; Deasy, Li et al. 2004; Peng and Huard 2004). Transplantation of autologous Bone Marrow derived cells in a rat model of blunt skeletal muscle trauma demonstrated its potential to improve functional outcome after skeletal muscle crush injury (Matziolis, Winkler et al. 2006). Nevertheless this approach suffers of the disadvantages associated with using an autologous source of cells and the discomfort associated with BM aspiration.

The therapeutic potential of the population of cells described herein in skeletal muscle regeneration was assessed in a rat model of blunt skeletal muscle trauma as described by (Matziolis, Winkler et al. 2006).

Experimental Protocol

Animals: Female Sprague Dawley rats about 12 weeks old 140-160 g—10 animals per group.

Rat Treatment: Crush of the soleus muscle.

Cells: Placental cells grown under 3D culture as described in WO2010/026575, which is hereby incorporated by reference in its entirety [hereafter "PLX cells"].

Cell preparation: Cryopreserved PLX cells were washed to remove DMSO and Albumin. Cells were resuspended in saline and diluted to the desired concentration (i.e., $5 \times 10^6$ in 40 µl).

Cell injection:
Immediately following injury (I)
1 week after muscle injury (DEL)
Cell dose: $2.5 \times 10^6$.
Injection volume: 20 µl
Functional muscle assessment: 3 weeks after treatment
Biopsies: 3 weeks after treatment Muscle Trauma The animals were anesthetized, and the left lower limb was shaved (Favorita II, Aesculap, Tuttlingen, Germany) and disinfected with povidone-iodine. Through a 2 cm posterolateral longitudinal incision of the skin and underlying fascia from the lateral gastrocnemius head to the Achilles tendon, the soleus muscle was mobilized and crushed bluntly. For this purpose a curved clamp with tips surrounded by polyethylene tubes was used to avoid lesions of the muscle fascia. The muscle was manually clamped seven times over its complete length with exception of the entry point of the supplying neurovascular structures, which arise from the mid part of the medial gastrocnemius. After multiple irrigations with saline solution, the superficial muscle and the skin were sutured.

Muscle Strength Measurement

The animals were re-anesthetized. The sciatic nerve and the soleus muscle were exposed bilaterally protecting all neurovascular structures. On the treated as well as on the uninjured side, the Achilles tendon was cut and the lower extremity was fixed into the muscle force measuring device (Fish, McKee et al. 1989; Racz, Illyes et al. 1997) (Experimetria, Budapest, Hungary). The distal part of the soleus muscle was connected to the force transducer through a suture (4-0, silk). All muscles that were inserted through the Achilles tendon, except the soleus muscle, were cut through closest to the Achilles tendon. The sciatic nerve was subsequently stimulated with 9 mA/75 Hz bipolar five times, 0.1 s each (8 periods) with 5 s intervals between the pulses. After this fast twitch stimulation, the maximal muscle strength was measured using a stimulation protocol of 9 mA/75 Hz for five times, 3 s each with 5 s intervals, reaching tetany in all cases. After termination of muscle strength measurements, the animals were sacrificed. Contraction forces under fast twitch ("FT") and tetanic ("TET") stimulation were compared for every muscle and visualized in two scatter plots (injured and uninjured muscles). All force values were normalized intra-individually versus the intact right control soleus muscles.

Figure 7:
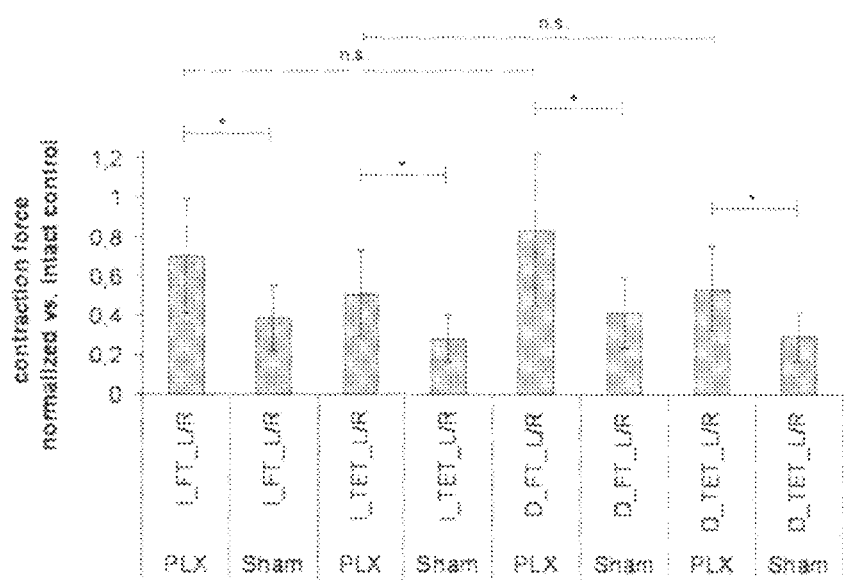
FIG. 7 shows the contraction force values in PLX treated ("PLX") and control ("Sham") rats. "I"—immediate transplant after trauma; "DEL"—transplant 7 days after trauma; "FT"—fast twitch contaction force; "TET"—titanic contraction force.

Results are shown in FIG. 7.

II. Effects of Human Placental Expanded (PLX) Cells on Inflammatory and Neuropathic Pain Chronic neuropathic pain is common in clinical practice. Patients with conditions as diverse as diabetic polyneuropathy, human immunodeficiency virus (HIV) sensory neuropathy, poststroke syndromes, ischemia, and multiple sclerosis frequently experience daily pain that greatly impairs their quality of life. Management of chronic pain remains a challenge in spite of numerous drugs that are either approved or still in development. Apart from inadequate relief, there are concerns about adverse effects and addiction (Dworkin, Backonja et al. 2003). During inflammation of peripheral tissues, numerous mediators are produced by endothelial cells, resident cells, and leucocytes that are recruited to the site of injury. Many of these mediators (e.g. protons, cytokines, and nerve growth factor) are known to elicit pain by activation of specialized primary afferent neurons called nociceptors (Rittner, Brack et al. 2008).

The potential of the population of cells described herein to reduce pain is examined in animal models for pain:

Experimental Protocol

Cells—Placental cells grown under 3D culture as described in WO2010/026575, which is hereby incorporated by reference in its entirety [hereafter "PLX cells"]

Animal Models

1—Chronic Inflammatory Model: Freund's adjuvant—Rats with peripheral inflammation induced by intraplantar injection of complete Freund's adjuvant (CFA). Complete Freund's adjuvant (CFA) administration to rodents produces a disease-like state that is believed to most closely resemble the human rheumatoid arthritis condition, which is characterized by inflammation of the membrane surrounding the joints as well as damage to the bone and cartilage. When administered into the base of the tail, a polyarthritic state develops in both hindpaws over several days with peak signs of inflammation, joint deterioration, and hyperalgesia occurring at approximately 3 weeks post-administration. This polyarthritic state can last several weeks (Cook and Nickerson 2005, which is hereby incorporated by reference in its entirety).

2—The Bennett Chronic Neuropathic Pain (partial ligation of the sciatic nerve, chronic constriction injury ("CCI") model) as described by Labuz et al. 2009 (Labuz, Schmidt et al. 2009, which is hereby incorporated by reference in its entirety).

Pain Assessment

Pain was assayed by measuring mechanical and thermal hyperalgesia and antinociception. Mechanical nociceptive thresholds were assessed using the paw pressure algesiometer (modified Randall-Selitto test; Ugo Basile; Brack, Rittner et al. 2004; Rittner, Labuz et al. 2006). On the day of testing, rats were held under paper wadding, and incremental pressure is applied via a wedgeshaped, blunt piston onto the dorsal surface of the hind paw by an automated gauge. The pressure required eliciting paw withdrawal, the paw pressure threshold (PPT), was determined by three consecutive trials separated by 10-s intervals. The same procedure was performed on the contralateral paw; the sequence of paws was alternated between subjects to preclude order effects. The treatments were randomized, and the experimenter was blinded to the treatment. A decrease in PPT was interpreted as hyperalgesia (pain), whereas a rise in PPT was interpreted as antinociception (analgesia). Thermal nociceptive thresholds were measured by the Hargreaves test (Rittner, Mousa et al. 2006). Animals were acclimatized to the testing apparatus. Radiant heat was applied to the plantar surface of a hind paw from underneath the glass floor with a high intensity light bulb, and paw withdrawal latency (PWL) was measured with an electronic timer (HTC Inc/Life Science, Woodland Hills, Calif.). The PWL was the average of two measurements taken with 20-s intervals. The stimulus intensity was adjusted to give a 9 to 10 s PWL in noninflamed paws, and the cutoff was 20 s to avoid tissue damage. A decrease in PWL was interpreted as hyperalgesia (pain), whereas a rise in PWL was interpreted as antinociception (analgesia).

Results

1. Inflammatory Pain Model (Rats)

We employed an inflammatory pain model in which rats receive a complete Freund's adjuvant (CFA; 150 µl) into right hind paw intraplantarly (i.pl.; into the plantar paw surface). Pain was measured with a paw pressure test to determine the paw pressure thresholds (PPT), while paw volume (PV; to estimate edema) was assessed with a plethysmometer.

Two days after CFA application rats were injected i.pl. as follows:
  Group 1: vehicle (100 µl)-4 rats
  Group 2: 1 million PLX cells in 100 µl—4 rats
  Group 3: 2 millions PLX cells in 100 µl—4 rats PPT and PV were measured immediately before CFA injection, then 2 days after CFA (and right afterwards rats received PLX cells) and then daily, starting 1 day after PLX cell injection (i.e. 3 days after CFA) until the 10th day following CFA, in both hind paws.

Figure 8A:
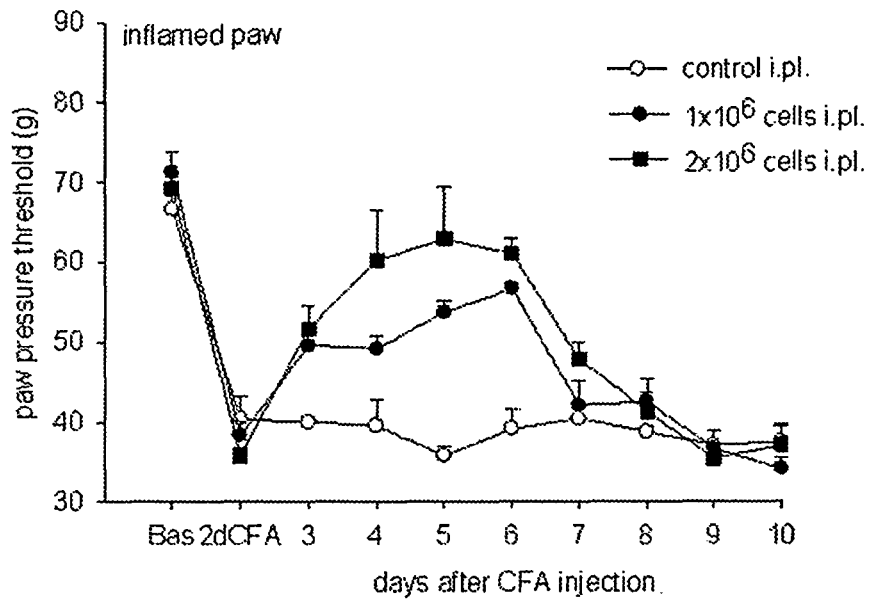
FIGS. 8A and 8B show the effects of PLX cells on inflammatory pain in the paw pressure test.
Figure 8B:
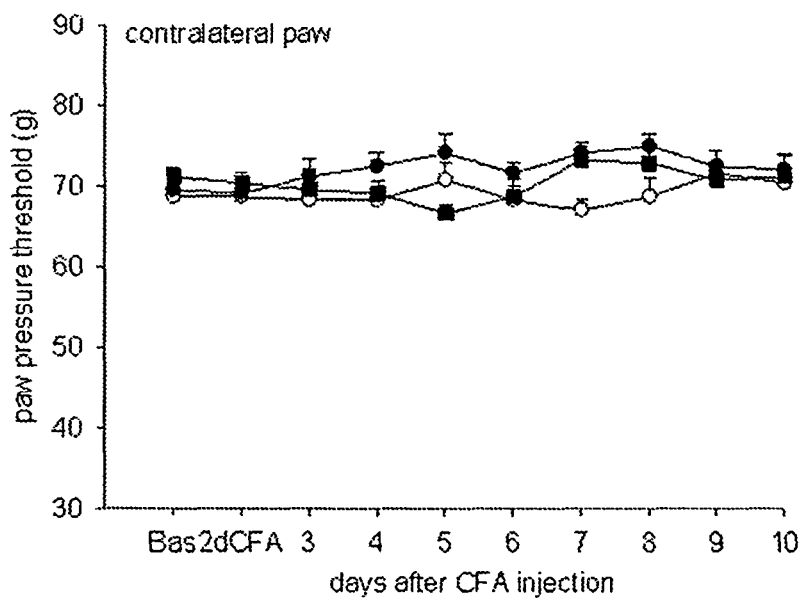
Figure 9A:
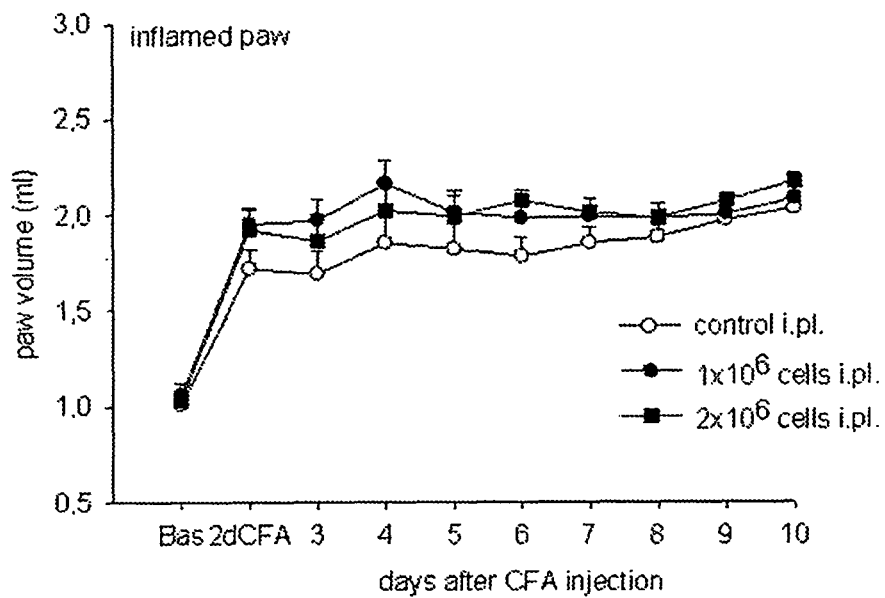
FIGS. 9A and 9B show paw volume plotted as a function of time following administration of PLX cells in the inflamed paw (FIG. 9A) and the contralateral paw (FIG. 9B).
Figure 9B:
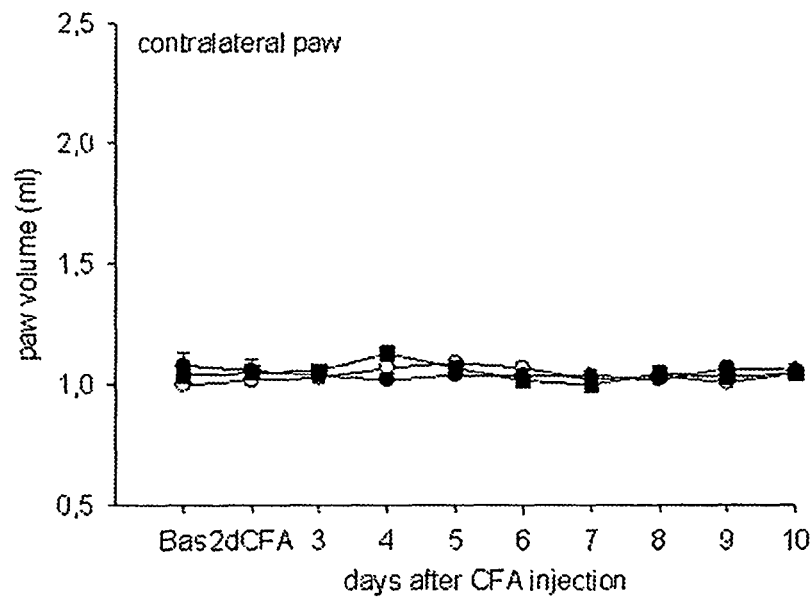

CFA injected i.pl. into one hind paw decreased the PPT in this paw from 2 days (2 d CFA) until 10 days as compared to the PPT before CFA injection (baseline; Bas) (FIG. 8). CFA did not change the PPT in contralateral paws (FIG. 8). PLX cells ($2\times10^6$) injected into inflamed paws seem to reverse the PPT to the level before CFA injection (FIG. 8A). PLX cells did not change the PPT in contralateral paws (FIG. 8B). PLX cells do not seem to alter paw edema (measured as PV) (FIGS. 9A and 9B).

2. Neuropathic Pain Model (Mice)

Two days following chronic constrictive injury ("CCI") animals were treated at the CCI site (i.e. at the site of nerve injury) according to the following groups:
  Group 1: vehicle (30 µl)—4 mice
  Group 2: 0.5 million PLX cells in 30 µl—4 mice
  Group 3: 1 million PLX cells in 30 µl—4 mice Mechanical and thermal sensitivities were assessed immediately before CCI (baseline; Bas), 2 days after CCI (2 d CCI; and right afterwards mice received PLX cells), then daily for 10 days (starting 1 day after PLX cell injection), and then at 14 and 21 days after CCI, in both hind paws.

Figure 10A:
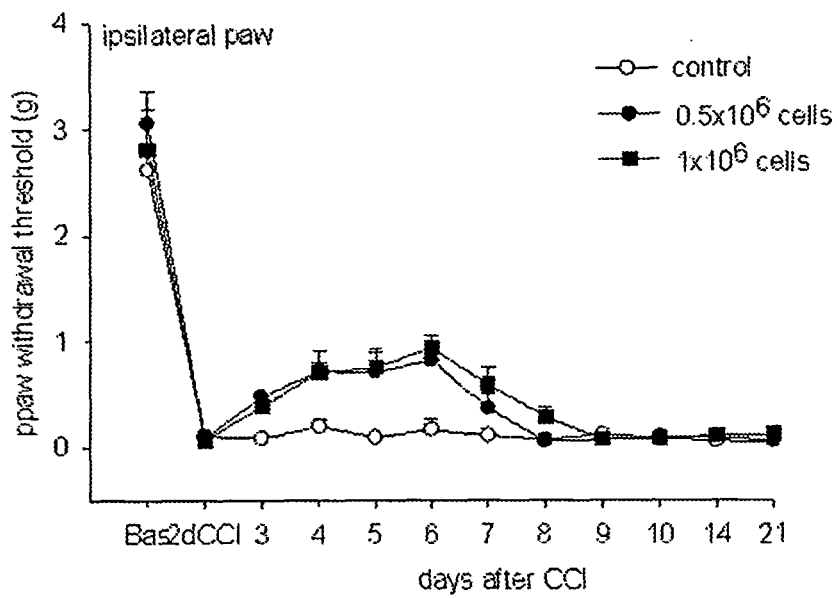
FIGS. 10A and 10B illustrate the effects of PLX cells on mechanical sensitivity (von Frey test) in neuropathic pain in the ipsilateral paw (FIG. 10A) and contralateral paw (FIG. 10B).
Figure 10B:
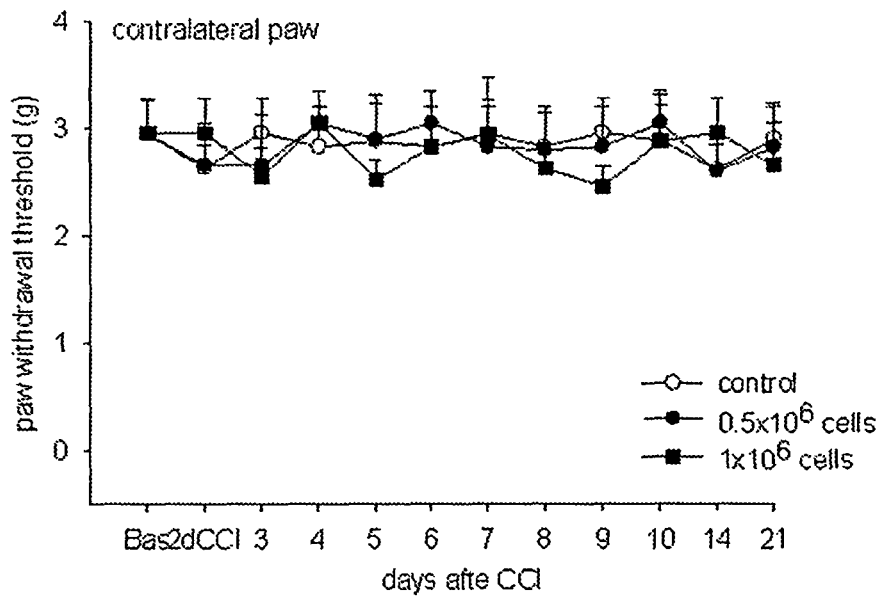
Figure 11A:
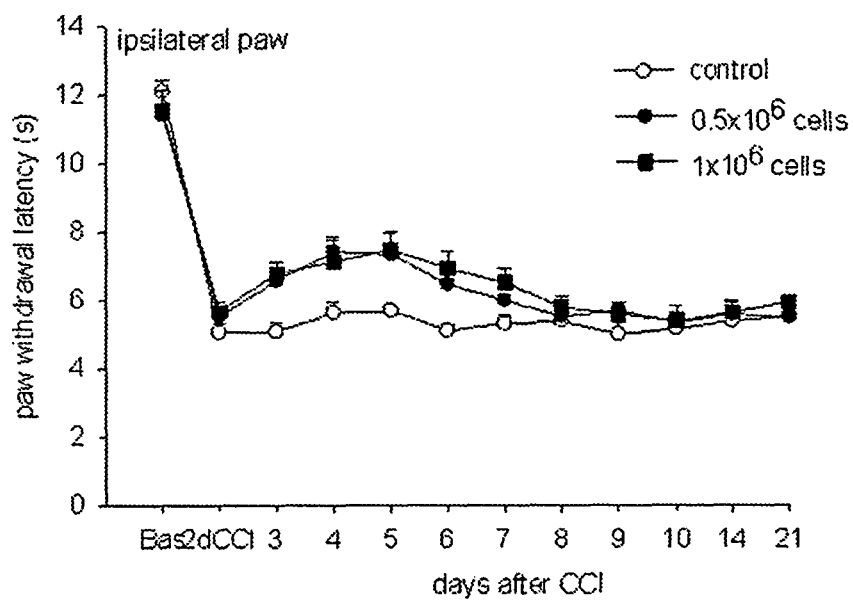
FIGS. 11A and 11B depict the effects of PLX cells on thermal sensitivity (Hargreaves test) in neuropathic pain in the ipsilateral paw (FIG. 11A) and contralateral paw (FIG. 11B).
Figure 11B:
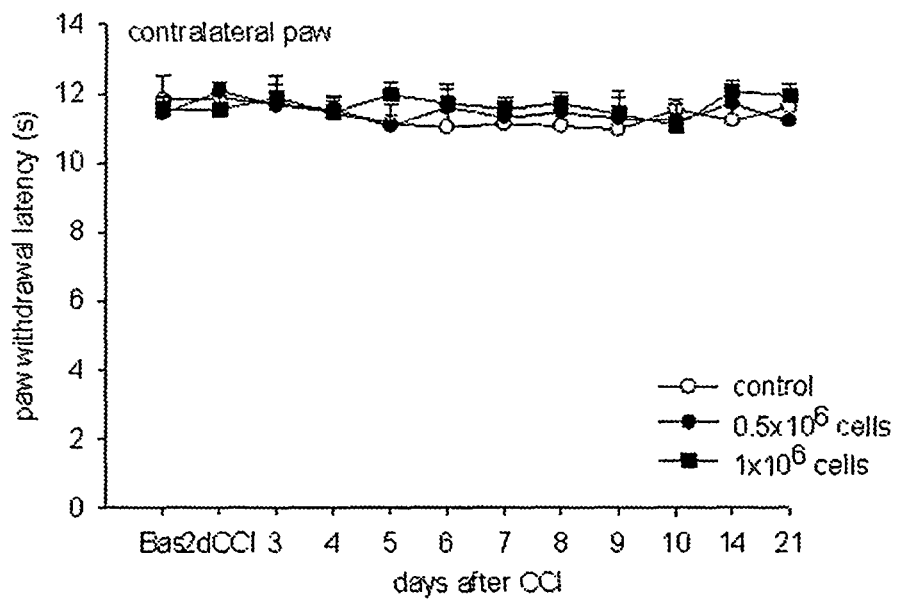
Figure 12A:
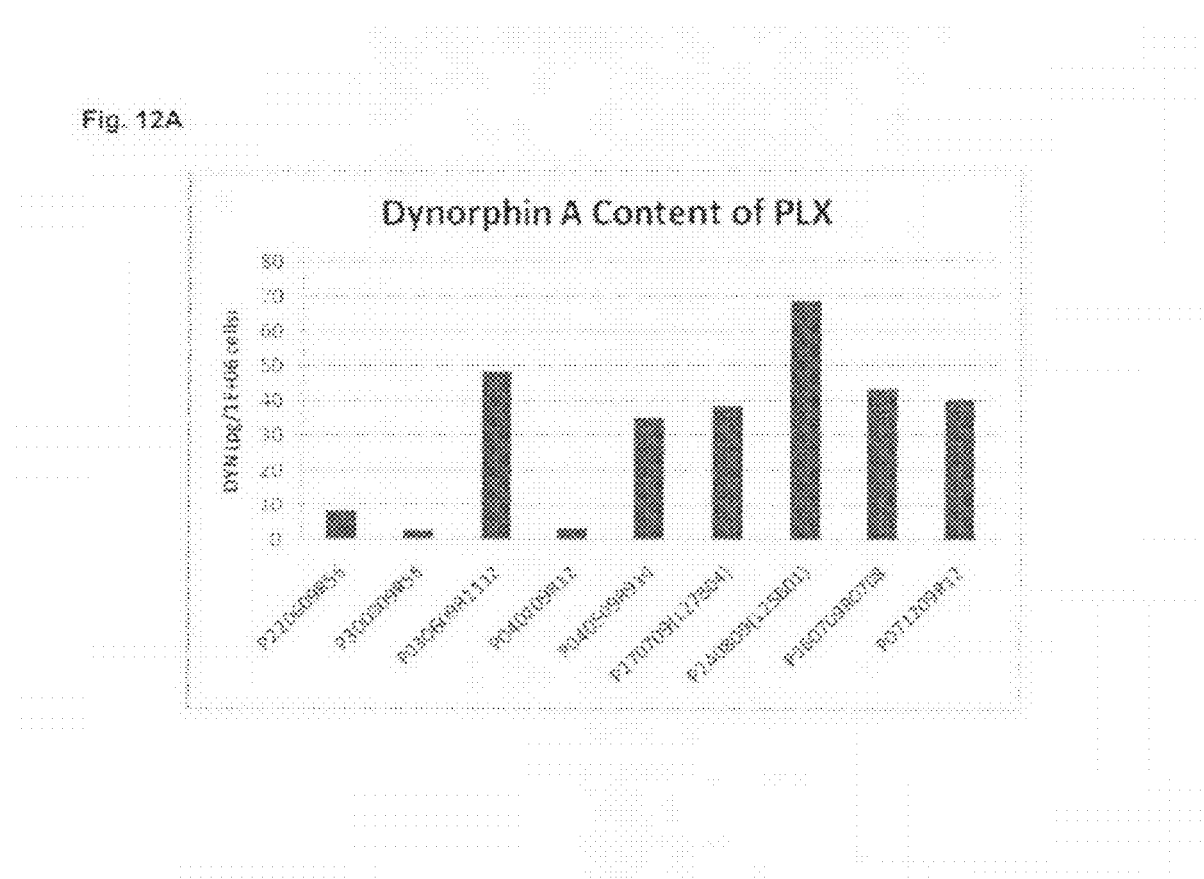
FIGS. 12A-E depict beta-Endorphin (FIG. 12A), dynorphin A (FIG. 12B), leu-enkephalin (FIG. 12C), met-enkephalin (FIG. 12D), and total (FIG. 12E) levels in 9 different PLX batches.
Figure 12B:
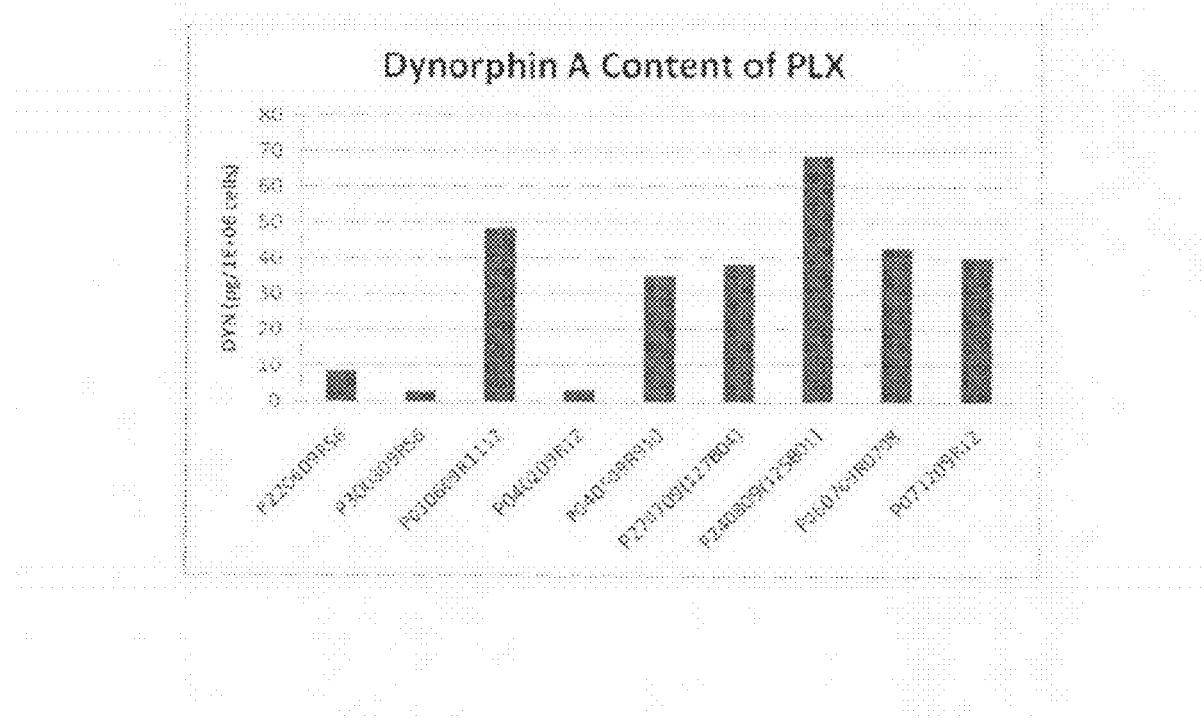
Figure 12C:
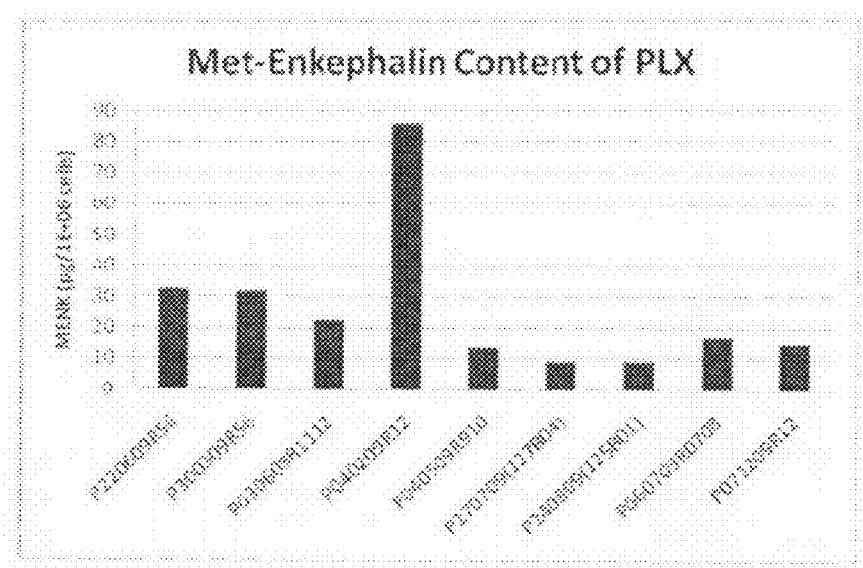
Figure 12D:
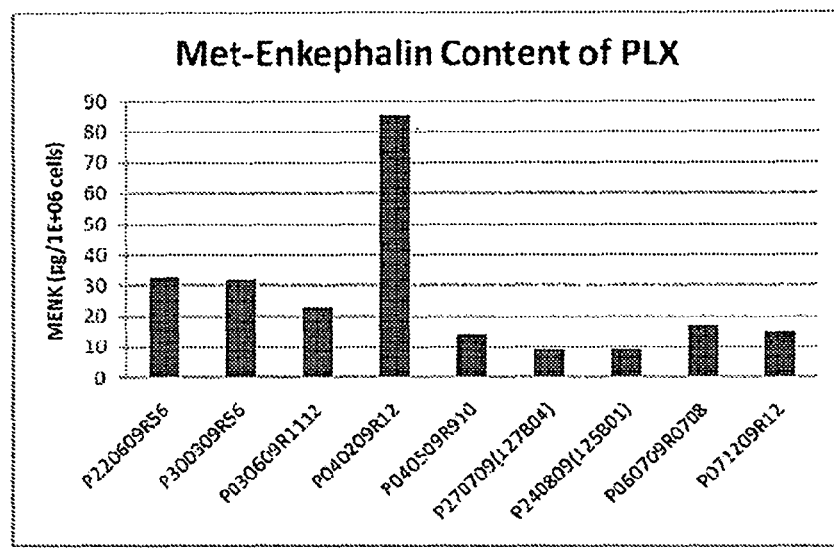
Figure 12E:
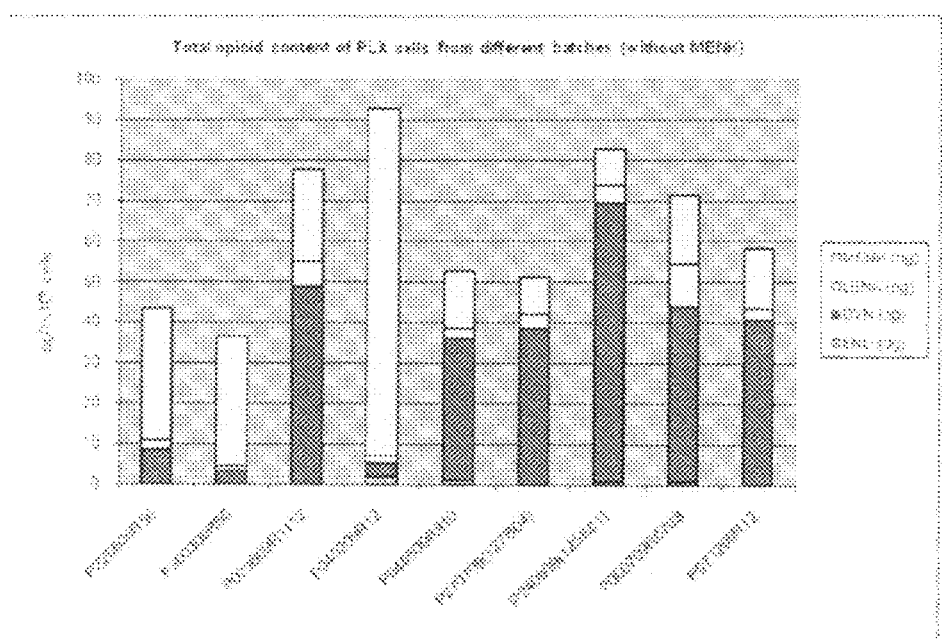

CCI of the sciatic nerve resulted in mechanical sensitivity (defined as decreased paw withdrawal thresholds) and thermal sensitivity (defined as lowered paw withdrawal latencies) in paws innervated by the injured paws but not in contralateral paws (FIGS. 10 and 11). PLX cells injected at the nerve injury site slightly attenuated both mechanical (FIG. 10A) and thermal (FIG. 11A) sensitivity. PLX cells did not produce alterations in contralateral paws (FIGS. 10B and 11B).

III. Endogenous Opioid Peptide Level in PLX Cells

The opioid peptide levels in PLX cells [that is, placental cells grown under 3D culture as described in WO2010/026575, which is hereby incorporated by reference in its entirety] were examined in attempt to assess whether the anti-nociception effect observed in the described neuropathic pain models was mediated by released opioids from the PLX cells.

Experimental Protocol

Cells were thawed, centrifuged to remove cryopreservation solution and resuspended in serum-free low glucose DMEM supplemented with 130 µM bestatin, 1 mM EDTA, and Roche Protease Inhibitor Cocktail Tablets Cat. No. 04 693 124 001 at a final concentration of $10\times10^6$ PLX cells/250 µl.

Measurement of opioid content was performed on three samples of $10\times10^6$ cells from each PLX batch—
  0.25 µl of a 10 mM ionomycin stock solution (final concentration is 10 µM) were added to cell suspension
  Cell suspension was shook for 5 min at 600 rpm and 37° C. in a heating block.
  Cell suspension was centrifuged (350×g/4° C.) and PLX cell pellets and supernatants were collected and stored at −20° C. until time of analysis.
  Opioid peptide amounts were determined using EIA kits (Phoenix Laboratories, Inc. and Peninsula Laboratories) as detailed below according to the manufacturer's instructions Kits for Detection of Opioid Peptides:
Enkephalin-Methionine—RIA Kit (Pensinsula Laboratories; #S-2119)
Enkephalin-Leucine—Fluorescent EIA Kit (Phoenix Laboratories Inc.; #FEK-024-21)
Dynorphin A—Fluorescent EIA Kit (Phoenix; #FEK-021-03)
Endorphin, beta—Fluorescent EIA Kit (Phoenix; #FEK-022-14)

Results

PLX cells contain beta-Endorphin, dynorphin A, leu-enkephalin and met-enkephalin at different levels. The level of each of these opioids was determined using the fluorescent EIA kits according to the manufacturer protocol (Phoenix Laboratories Inc.). $10^7$ cells from each batch were examined. Levels of these opioids in 9 different PLX batches are presented in FIGS. 12A-E.

IV. Cell Therapy for Myocardial Regeneration in Unloaded Hearts: an Experimental Model of Mechanical Assisted Device Therapy Heart failure (HF) affects a rapidly growing population of patients. Despite improvements in the understanding and therapy of many stages of cardiovascular disease, there has been little progress in treating HF. In end-stage heart failure, mechanical ventricular assist devices (VAD) are being used as bridge-to-transplantation, as a bridge-to-recovery, or as the definitive therapy. The therapeutic effect of population of cells described herein in increasing the efficacy of VAD support is tested in an animal model of myocardial infarction (MI). The usual model for acute MI is the mouse, by ligation of the left anterior descending coronary artery (LAD) (Kolk, Meyberg et al. 2009), providing a useful and convenient tool for the research in ischemic heart disease.

Experimental Protocol

Disease model—myocardial infarction by LAD ligation

Animal Strain—Balb/C, male, 6-8 weeks

Total number of mice—15

Distribution of mice between different experimental groups

Early (DAY 3) experimental group (PLX)—3

Late (DAY 28) experimental group (PLX)—6

Late (DAY 28) control group (infarct, only vehicle)—6

Dosage of cells/mice—1×10$^6$

Cells/vial—1×10$^6$

Anaesthesia used—Ketamine-xylaxine

Experimental Procedures

Day 0—LAD ligation and injection of cells in 100-150 µl of PBS (without Ca, Mg)

Day 1—1$^{st}$ echocardiography (all 3 groups),

Day 3—sacrifice 3 early group mice (PLX) and subject them to sectioning looking for Human nuclear antigen (hNuc).

Day 7—2$^{nd}$ echocardiography (both late groups)

Day 14—3$^{rd}$ echocardiography (both late groups)

Day 21—4$^{th}$ echocardiography (both late groups)

Day 28—5$^{th}$ echocardiography (both late groups), MRI (both late groups)

Mice will be sacrificed at the end of the four weeks followed by the excision of the hearts. Some of the hearts would be used for RNA isolation and others will be subject to paraffin sectioning for the assessment of fine structures and cryosectioning for the detection of cardiac specific markers.

Marker Profile for Immunohistochemistry:

1. Human nuclear antigen (hNuc)—at the early stage (DAY 3)

2. Cardiac myosin heavy chain

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCE LIST

Other References are Cited in the Application

Ajmo C. T., Jr., Vernon D. O., Collier L., Hall A. A., Garbuzova-Davis S., Willing A. and Pennypacker K. R., The spleen contributes to stroke-induced neurodegeneration, J, Neurosci. Res. 86 (2008) 2227-2234.

Arcila, M. E., B. T. Ameredes, et al. (1997). "Mass and functional capacity of regenerating muscle is enhanced by myoblast transfer." J Neurobiol 33(2): 185-98.

Bach, A. D., J. P. Beier, et al. (2004). "Skeletal muscle tissue engineering." J Cell Mol Med 8(4): 413-22.

Bliss T., Guzman R., Daadi M. and Steinberg G. K., Cell transplantation therapy for stroke, Stroke 38 (2007) 817-826.

Brack, A., H. L. Rittner, et al. (2004). "Control of inflammatory pain by chemokine-mediated recruitment of opioid-containing polymorphonuclear cells." Pain 112(3): 229-38.

Chang C. J., Yen M. L., Chen Y. C., Chien C. C., Huang H. I., Bai C. H. and Yen B. L., Placenta-derived multipotent cells exhibit immunosuppressive properties that are enhanced in the presence of interferon-gamma, Stem Cells 24 (2006) 2466-2477.

Chen J., Li Y., Katakowski M., Chen X., Wang L., Lu D., Lu M., Gautam S. C. and Chopp M., Intravenous bone marrow stromal cell therapy reduces apoptosis and promotes endogenous cell proliferation after stroke in female rat, J. Neurosci. Res. 73 (2003) 778-786.

Chen J., Sanberg P. R., Li Y., Wang L., Lu M., Willing A. E., Sanchez-Ramos J, and Chopp M., Intravenous administration of human umbilical cord blood reduces behavioral deficits after stroke in rats, Stroke 32 (2001) 2682-2688.

Chopp M. and Li Y., Treatment of neural injury with marrow stromal cells, Lancet Neurol. 1 (2002) 92-100.

Cook, C. D. and M. D. Nickerson (2005). "Nociceptive sensitivity and opioid antinociception and antihyperalgesia in Freund's adjuvant-induced arthritic male and female rats." J Pharmacol Exp Ther 313(1): 449-59.

Deasy, B. M., Y. Li, et al. (2004). "Tissue engineering with muscle-derived stem cells." Curr Opin Biotechnol 15(5): 419-23.

DeRosimo, J. F., C. H. Washabaugh, et al. (2000). "Enhancement of adult muscle regeneration by primary myoblast transplantation." Cell Transplant 9(3): 369-77.

Dong Y. and Benveniste E. N., Immune function of astrocytes, Glia 36 (2001) 180-190.

Dworkin, R. H., M. Backonja, et al. (2003). "Advances in neuropathic pain: diagnosis, mechanisms, and treatment recommendations." Arch Neurol 60(11): 1524-34.

Faulkner J. R., Herrmann J. E., Woo M. J., Tansey K. E., Doan N. B. and Sofroniew M. V., Reactive astrocytes protect tissue and preserve function after spinal cord injury, J. Neurosci. 24 (2004)2143-2155.

Fish, J. S., N. H. McKee, et al. (1989). "Isometric contractile function recovery following tourniquet ischemia." J Surg Res 47(4): 365-70.

Gao Q, Li Y. and Chopp M., Bone marrow stromal cells increase astrocyte survival via upregulation of phosphoinositide 3-kinase/threonine protein kinase and mitogen-activated protein kinase kinase/extracellular signal-regulated kinase pathways and stimulate astrocyte trophic factor gene expression after anaerobic insult, Neuroscience 136 (2005) 123-134.

Himeda T., Tounai H., Hayakawa N. and Araki T., Postischemic alterations of BDNF, NGF, HSP 70 and ubiquitin immunoreactivity in the gerbil hippocampus: pharmacological approach, Cell Mol. Neurobiol. 27 (2007) 229-250.

Hu J., Ferreira A, and Van Eldik L. J., S100beta induces neuronal cell death through nitric oxide release from astrocytes, J. Neurochem. 69 (1997) 2294-2301.

Huard, J., B. Cao, et al. (2003). "Muscle-derived stem cells: potential for muscle regeneration." Birth Defects Res C Embryo Today 69(3): 230-7.

Hum P. D., Subramanian S., Parker S. M., Afentoulis M. E., Kaler L. J., Vandenbark A. A. and Offner H., T- and B-cell-deficient mice with experimental stroke have reduced lesion size and inflammation, J. Cereb. Blood Flow Metab 27 (2007) 1798-1805.

In't Anker P. S., Scherjon S. A., Kleijburg-van der K. C., de Groot-Swings G. M., Claas F. H., Fibbe W. E, and Kanhai H. H., Isolation of mesenchymal stem cells of fetal or maternal origin from human placenta, Stem Cells 22 (2004) 1338-1345.

Irintchev, A., M. Langer, et al. (1997). "Functional improvement of damaged adult mouse muscle by implantation of primary myoblasts." J Physiol 500 (Pt 3): 775-85.

Jones B. J., Brooke G., Atkinson K. and McTaggart S. J., Immunosuppression by placental indoleamine 2,3-dioxygenase: a role for mesenchymal stem cells, Placenta 28 (2007) 1174-1181.

Kamelger, F. S., R. Marksteiner, et al. (2004). "A comparative study of three different biomaterials in the engineering of skeletal muscle using a rat animal model." Biomaterials 25(9): 1649-55.

Kolk, M. V., D. Meyberg, et al. (2009). "LAD-ligation: a murine model of myocardial infarction." J Vis Exp (32).

Kundrotiene J., Wagner A. and Liljequist S., Extradural compression of sensorimotor cortex: a useful model for studies on ischemic brain damage and neuroprotection, J. Neurotrauma 19 (2002) 69-84.

Labuz, D., Y. Schmidt, et al. (2009). "Immune cell-derived opioids protect against neuropathic pain in mice." J Clin Invest 119(2): 278-86.

Le Blank K., Immunomodulatory effects of fetal and adult mesenchymal stem cells, Cytotherapy. 5 (2003) 485-489.

Lee M. Y., Deller T., Kirsch M., Frotscher M. and Hofmann H. D., Differential regulation of ciliary neurotrophic factor (CNTF) and CNTF receptor alpha expression in astrocytes and neurons of the fascia dentata after entorhinal cortex lesion, J. Neurosci. 17 (1997) 1137-1146.

Li, Y. and J. Huard (2002). "Differentiation of muscle-derived cells into myofibroblasts in injured skeletal muscle." Am J Pathol 161(3): 895-907.

Li Y., Chen J., Chen X. G., Wang L., Gautam S. C., Xu Y. X., Katakowski M., Zhang L J., Lu M., Janakiraman N. and Chopp M., Human marrow stromal cell therapy for stroke in rat: neurotrophins and functional recovery, Neurology 59 (2002) 514-523.

Liberto C M., Albrecht P. J., Herx L. M., Yong V. W. and Levison S. W., Pro-regenerative properties of cytokine-activated astrocytes, J, Neurochem. 89 (2004) 1092-1100.

Marti H. H. and Risau W., Systemic hypoxia changes the organ-specific distribution of vascular endothelial growth factor and its receptors, Proc. Natl. Acad. Sci. U.S. A 95 (1998) 15809-15814.

Matziolis, G., T. Winkler, et al. (2006). "Autologous bone marrow-derived cells enhance muscle strength following skeletal muscle crush injury in rats." Tissue Eng 12(2): 361-7.

Nishishita T., Ouchi K., Zhang X., Inoue M., Inazawa T., Yoshiura K., Kuwabara K., Nakaoka T., Watanabe N., Igura K., Takahashi T A. and Yamashita N., A potential pro-angiogenic cell therapy with human placenta-derived mesenchymal cells, Biochem. Biophys. Res. Commun. 325 (2004) 24-31.

Okawa H., Okuda O., Arai H., Sakuragawa N. and Sato K., Amniotic epithelial cells transform into neuron-like cells in the ischemic brain, Neuroreport 12 (2001) 4003-4007.

Peng, H. and J. Huard (2004). "Muscle-derived stem cells for musculoskeletal tissue regeneration and repair." Transpl Immunol 12(3-4): 311-9.

Prather W. R., Toren A. and Meiron M., Placental-derived and expanded mesenchymal stromal cells (PLX-I) to enhance the engraftment of hematopoietic stem cells derived from umbilical cord blood, Expert. Opin. Biol. Ther. 8 (2008) 1241-1250.

Prather W. R., Toren A., Meiron M., Ofir R., Tschope C. and Horwitz E. M., The role of placental-derived adherent stromal cell (PLX-PAD) in die treatment of critical limb ischemia, Cytotherapy. 11(4) (2009) 427-434.

Racz, J. B., G. Illyes, et al. (1997). "The functional and morphological damage of ischemic reperfused skeletal muscle." Eur Surg Res 29(4): 254-63.

Rittner, H. L., A. Brack, et al. (2008). "Pain and the immune system." Br J Anaesth 101(1): 40-4.

Rittner, H. L., D. Labuz, et al. (2006). "Pain control by CXCR2 ligands through Ca2+-regulated release of opioid peptides from polymorphonuclear cells." FASEB J 20(14): 2627-9.

Rittner, H. L., S. A. Mousa, et al. (2006). "Selective local PMN recruitment by CXCL1 or CXCL2/3 injection does not cause inflammatory pain." J Leukoc Biol 79(5): 1022-32.

Roelen D. L., van der Mast B. J., in't Anker P. S., Kleijburg C, Eikmans M., van B. E., de Groot-Swings G. M., Fibbe W. E., Kanhai H. H., Scherjon S. A. and Claas F. H., Differential immunomodulatory effects of fetal versus maternal multipotent stromal cells, Hum. Immunol. 70 (2009) 16-23.

Saxena, A. K., J. Marler, et al. (1999). "Skeletal muscle tissue engineering using isolated myoblasts on synthetic biodegradable polymers: preliminary studies." Tissue Eng 5(6): 525-32

Schabitz W. R., Berger C, Kollmar R., Seitz M., Tanay E., Kiessling M., Schwab S. and Sommer C., Effect of brain-derived neurotrophic factor treatment and forced arm use on functional motor recovery after small cortical ischemia, Stroke 35 (2004) 992-997.

Shen L. H., Li Y., Chen J., Zacharek A., Gao Q., Kapke A., Lu M., Raginski K., Vanguri P., Smith A. and Chopp M., Therapeutic benefit of bone marrow stromal cells administered 1 month after stroke, J. Cereb. Blood Flow Metab 27 (2007) 6-13.

Silver J. and Miller J. H., Regeneration beyond the glial scar, Nat. Rev. Neurosci. 5 (2004) 146-156.

Strachan R. D., Kane P. J., Cook S., Chambers I. R., Clayton C. B. and Mendelow A. D., Immunosuppression by wholebody irradiation and its effect on oedema in experimental cerebral ischaemia, Acta Neurol. Scand. 86 (1992) 256-259.

Tamura A., Graham D. I., McCulloch J. and Teasdale G. M., Focal cerebral ischaemia in the rat: 1. Description of technique and early neuropathological consequences following middle cerebral artery occlusion, J. Cereb. Blood Flow Metab 1 (1981) 53-60.

Toyama K., Honmou O., Harada K, Suzuki J., Houkin K., Hamada H. and Kocsis J. D., Therapeutic benefits of angiogenetic gene-modified human mesenchymal stem cells after cerebral ischemia, Exp. Neurol. 216 (2009) 47-55.

Trendelenburg G. and Dimagl U., Neuroprotective role of astrocytes in cerebral ischemia: focus on ischemic preconditioning, Glia 50 (2005) 307-320.

Wei O. Y., Huang Y. L., Da C D. and Cheng J. S., Alteration of basic fibroblast growth factor expression in rat during cerebral ischemia, Acta Pharmacol. Sin. 21 (2000) 296-300.

Yen B. L., Huang Hi., Chien C. C., Jui Ko B. S, Yao M., Shun C. T., Yen M. L., Lee M X. and Chen Y. C., Isolation of multipotent cells from human term placenta, Stem Cells 23 (2005) 3-9.

Zhao M. Z., Nonoguchi N., Ikeda N., Watanabe T., Furutama D., Miyazawa D., Funakoshi H., Kajimoto Y., Nakamura T., Dezawa M., Shibata M. A., Otsuki Y., Coffin R. S., Liu W. D., Kuroiwa T. and Miyatake S., Novel therapeutic strategy for stroke in rats by bone marrow stromal cells and ex vivo HGF gene transfer with HSV-1 vector, J. Cereb. Blood Flow Metab 26 (2006) 1176-1188.

Zhu H., Mitsuhashi N., Klein A., Barsky L. W., Weinberg K., Barr M. L., Demetriou A. and Wu G. D., The role of the hyaluronan receptor CD44 in mesenchymal stem cell migration in the extracellular matrix, Stem Cells 24 (2006) 928-935.

What is claimed is:

1. A composition comprising:
   (a) a population of adherent cells isolated from a placenta, cultured under three-dimensional culturing conditions promoting cell expansion, and harvested from said three-dimensional culturing conditions, wherein the population comprises at least 70% adherent cells from a maternal portion of the placenta, wherein the maternal portion of the placenta is either or both of decidua basalis or decidua parietalis, and wherein the adherent cells do not differentiate into osteogenic or adipogenic lineages when subjected to the same differentiation-inducing conditions as cells derived from bone marrow that differentiate into said lineages; and
   (b) an artificial freezing mixture in an amount effective for cryopreservation and subsequent thawing of viable adherent cells.

2. The composition of claim 1, wherein not more than 3.5% of the population of adherent cells express CD200.

3. The composition of claim 1, wherein said adherent cells express one or more of CD73, CD90, CD29, CD105 or D7-fib.

4. The composition of claim 1, wherein said adherent cells do not express CD3, CD4, CD45, CD80, HLA-DR, CD11b, CD19, CD34, CD31, CD200, KDR, or CD79.

5. The composition of claim 1, wherein said adherent cells comprise a cell diameter which is smaller than that of adherent cells derived from a fetal portion of placenta.

6. The composition of claim 1, wherein said adherent cells comprise a cell proliferation capacity which is higher than that of adherent cells derived from a fetal portion of placenta.

7. The composition of claim 1, wherein the freezing mixture comprises dimethyl sulfoxide (DMSO).

8. The composition of claim 1, wherein the composition is contained in a cryopreservation vial.

9. The composition of claim 1, wherein the composition is frozen.

10. The composition of claim 9, wherein the composition is frozen in liquid nitrogen.

11. A method of treating a medical condition in a subject in need thereof comprising administering to the subject a therapeutically effective amount of a population of cells obtained from the composition of claim 1, thereby treating the subject, wherein the condition is selected from the group consisting of ischemia, peripheral arterial disease (PAD), critical limb ischemia (CLI), lower extremity ischemia, stroke, ischemic vascular disease, vascular disease of the kidney, ischemic heart disease, myocardial ischemia, coronary artery disease (CAD), atherosclerotic cardiovascular disease, left main coronary artery disease, arterial occlusive disease, peripheral ischemia, peripheral vascular disease, arteriosclerosis, retinopathy, retinal repair, remodeling disorder, von Hippel-Lindau syndrome, hereditary hemorrhagic telangiectasia ischemic vascular disease, Buerger's disease, ischemic renal disease, ischemic placenta, reproduction associated disorders, graft-versus-host disease, solid organ transplantation, hematopoietic stem cell transplantation, diabetes, connective tissue damage, cancer, pre-cancer, bone cancer, osteosarcoma, bone metastases, bone fracture, burn wound, articular cartilage defect, deep wound, delayed wound-healing, delayed ulcer healing, subchondral-bone cyst, osteoporosis, osteoarthritis, degenerated bone, cartilage damage, articular cartilage defect, injured tendons, autoimmune diseases, metabolic disorders, psoriasis, neuropathic pain, peripheral nerve injury, neurodegenerative disease, support of kidney transplantation and inflammatory diseases.

12. The method of claim 11, wherein the condition is heart failure, myocardial infarction, neuropathic pain, skeletal muscle defect, stroke, or ischemic heart disease.

13. The method of claim 12, wherein the condition is skeletal muscle defect.

14. The method of claim 12, wherein the condition is myocardial infarction.

15. The method of claim 12, wherein the condition is neuropathic pain.

16. The method of claim 15, wherein the neuropathic pain is associated with inflammatory pain, diabetic polyneuropathy, human immunodeficiency virus (HIV) sensory neuropathy, post-stroke syndromes, ischemia, or multiple sclerosis.

17. The method of any one of claims 13, 15, or 14, wherein said adherent cells express one or more of CD73, CD90, CD29, CD105 or D7-fib.

18. The method of any one of claims 13, 15, or 14, wherein said adherent cells do not express CD3, CD4, CD45, CD80, HLA-DR, CD11b, CD14, CD19, CD34, CD31, CD200, CD271, KDR, or CD79.

19. The method of any one of claims 13, 15, or 14, wherein said adherent cells express one or more of beta-Endorphin, dynorphin A, leuenkephalin, or met-enkephalin.

20. The method of any one of claims 13, 15, or 14, wherein said adherent cells comprise at least 70% adherent cells from a maternal portion of the placenta.

21. The method of claim 20, wherein not more than 3.5% of the adherent cells express CD200.

* * * * *

UNITED STATES PATENT AND TRADEMARK OFFICE
CERTIFICATE OF CORRECTION

PATENT NO.        : 9,175,262 B2
APPLICATION NO.   : 13/512503
DATED             : November 3, 2015
INVENTOR(S)       : Zami Aberman Page 1 of 1

It is certified that error appears in the above-identified patent and that said Letters Patent is hereby corrected as shown below:

On the title page item (73), should read as shown below:

Assignee:    Pluristem Ltd., Haifa (IL)

Signed and Sealed this
Twenty-third Day of February, 2016

Michelle K. Lee
*Director of the United States Patent and Trademark Office*